US011315381B2

(12) United States Patent
Greyshock et al.

(10) Patent No.: US 11,315,381 B2
(45) Date of Patent: Apr. 26, 2022

(54) APPARATUSES, SYSTEMS, AND METHODS FOR THE AUTOMATED DISPENSING OF ARTICLES

(71) Applicant: OMNICELL, INC., Mountain View, CA (US)

(72) Inventors: Shawn T. Greyshock, Tarentum, PA (US); Patrick Joseph Braun, Pittsburgh, PA (US); William B. Pattison, Mars, PA (US)

(73) Assignee: OMNICELL, INC., Mountain View, CA (US)

( * ) Notice: Subject to any disclaimer, the term of this patent is extended or adjusted under 35 U.S.C. 154(b) by 105 days.

(21) Appl. No.: 16/775,863

(22) Filed: Jan. 29, 2020

(65) Prior Publication Data

US 2020/0168023 A1    May 28, 2020

Related U.S. Application Data

(63) Continuation of application No. 15/719,671, filed on Sep. 29, 2017, now Pat. No. 10,586,418.

(51) Int. Cl.
*G16H 20/13* (2018.01)
*G07F 11/16* (2006.01)
(Continued)

(52) U.S. Cl.
CPC .......... *G07F 11/1657* (2020.05); *G07F 9/002* (2020.05); *G07F 11/1653* (2020.05);
(Continued)

(58) Field of Classification Search
CPC ... G07F 17/0092; G07F 11/165; G16H 20/13; B65B 5/067
(Continued)

(56) References Cited

U.S. PATENT DOCUMENTS 2,805,898 A    9/1957 Willis, Jr.
3,552,090 A    1/1971 Roberts et al.
(Continued)

FOREIGN PATENT DOCUMENTS

CN    101917956 A    12/2010
CN    101996447 A    3/2011
(Continued)

OTHER PUBLICATIONS

Office Action for Japanese Patent Application No. 2020-517987 dated Apr. 1, 2021.
(Continued)

*Primary Examiner* — Timothy R Waggoner
(74) *Attorney, Agent, or Firm* — Alston & Bird LLP

(57) ABSTRACT

Provided herein is a system for automated dispensing of articles. Systems may include: a robotic arm; an end-of-arm tool attached to the robotic arm; a scanning device proximate the end-of-arm tool; and a controller to control the robotic arm and the end-of-arm tool. The end-of-arm tool may include a body and two or more vacuum cups extending from the body, where the controller controls a level of suction provided to each of the two or more vacuum cups individually. Each of the two or more vacuum cups extending from the body may be movable between a retracted position proximate the body, and an extended position away from the body of the end-of-arm tool in response to instruction from the controller. Suction may be provided only to the vacuum cups of the two or more vacuum cups that are disposed in the extended position.

21 Claims, 30 Drawing Sheets

(51) Int. Cl.
  *G07F 11/42* (2006.01)
  *G07G 1/00* (2006.01)
  *G07F 9/00* (2006.01)
  *G07F 11/60* (2006.01)
  *A61J 7/00* (2006.01)
  *G06K 7/10* (2006.01)

(52) U.S. Cl.
  CPC .............. *G07F 11/42* (2013.01); *G07F 11/60* (2013.01); *G07G 1/0045* (2013.01); *G16H 20/13* (2018.01); *A61J 7/0069* (2013.01); *A61J 7/0076* (2013.01); *A61J 2205/10* (2013.01); *A61J 2205/60* (2013.01); *G06K 7/10366* (2013.01); *G06K 7/10861* (2013.01)

(58) Field of Classification Search
  USPC .................................................. 700/236–244
  See application file for complete search history.

(56) References Cited

U.S. PATENT DOCUMENTS

| | | |
|---|---|---|
| 23,624,782 | 11/1971 | McPeek |
| 3,761,134 A | 9/1973 | Hurd |
| 4,202,153 A | 5/1980 | Lerner |
| 4,203,269 A * | 5/1980 | Petersen .................. B65B 5/067 53/258 |
| 4,393,640 A | 7/1983 | Cole |
| 5,468,110 A | 11/1995 | McDonald et al. |
| 6,330,351 B1 | 12/2001 | Yasunaga |
| 6,516,587 B1 | 2/2003 | Chikatani |
| 6,601,707 B2 | 8/2003 | DeSmedt |
| 6,994,409 B2 * | 2/2006 | Godlewski ............. A47B 63/06 312/215 |
| 7,513,716 B2 | 4/2009 | Hayashi |
| 7,654,064 B2 | 2/2010 | Riccardi |
| 7,748,199 B2 | 7/2010 | Sankaran |
| 8,191,719 B2 | 6/2012 | Van Ooyen et al. |
| 8,252,232 B2 * | 8/2012 | Neeper .............. G01N 35/0099 422/65 |
| 8,483,867 B2 | 7/2013 | Braun et al. |
| 10,294,029 B2 * | 5/2019 | Joplin ................... B65B 7/2842 |
| 10,586,418 B2 | 3/2020 | Greyshock |
| 2004/0255556 A1 | 12/2004 | Boal |
| 2006/0184271 A1 | 8/2006 | Loveless |
| 2010/0030667 A1 * | 2/2010 | Chudy .................. G06Q 10/08 705/28 |
| 2010/0042255 A1 | 2/2010 | Boutin |
| 2010/0051187 A1 | 3/2010 | Willick et al. |
| 2011/0024444 A1 | 2/2011 | Braun |
| 2012/0029687 A1 * | 2/2012 | Hagen ................. B65G 1/0407 700/218 |
| 2013/0061556 A1 | 3/2013 | Hatsuno |
| 2013/0126547 A1 * | 5/2013 | Kim ...................... G07F 11/26 221/69 |
| 2013/0287537 A1 | 10/2013 | Hecht et al. |
| 2014/0058555 A1 * | 2/2014 | Rhoads, Jr .............. G07F 11/30 700/215 |
| 2014/0108028 A1 | 4/2014 | Braun |
| 2014/0116013 A1 * | 5/2014 | Doke ..................... B65B 5/067 53/473 |
| 2014/0262690 A1 | 9/2014 | Henderson et al. |
| 2015/0308466 A1 | 10/2015 | Girtman et al. |
| 2016/0327941 A1 | 11/2016 | Stiernagle et al. |
| 2017/0166407 A1 | 6/2017 | Singh et al. |
| 2017/0203867 A1 | 7/2017 | Shook |
| 2017/0246083 A1 | 8/2017 | Amano et al. |
| 2018/0305125 A1 | 10/2018 | Guo et al. |
| 2019/0102965 A1 | 4/2019 | Greyshock |

FOREIGN PATENT DOCUMENTS

| | | |
|---|---|---|
| CN | 206 358 922 U | 7/2017 |
| CN | 206 375 266 U | 8/2017 |
| DE | 2139470 A1 | 4/1972 |
| EP | 0447012 A1 | 9/1991 |
| EP | 2645298 A1 | 10/2013 |
| FR | 2057265 A5 | 5/1971 |
| GB | 201520079 | 5/2017 |
| JP | 5-19213 | 3/1993 |
| JP | 5-208716 | 8/1993 |
| JP | 2001-054886 A | 2/2001 |
| JP | 2003-305676 A | 10/2003 |
| JP | 2013-133220 A | 7/2013 |
| JP | 2015039767 | 3/2015 |
| KR | 10-2013-0030526 A | 3/2013 |
| WO | WO 2017/081281 A1 | 5/2017 |
| WO | WO-2019/067174 A1 | 4/2019 |

OTHER PUBLICATIONS

U.S. Appl. No. 15/719,671, filed Sep. 29, 2017, 2019/0102965 A1, Allowed.
International Search Report and Written Opinion for Application No. PCT/US2018/049588 dated Feb. 20, 2019, 15 pages.
Office Action for U.S. Appl. No. 15/719,671 dated Jul. 12, 2019.
Office Action for U.S. Appl. No. 15/719,671 dated Feb. 4, 2019.
Notice of Allowance for U.S. Appl. No. 15/719,671 dated Oct. 30, 2019.
1st Office Action for China Application No. 2018800615271 dated Jun. 3, 2021 (13 pages).
Final Office Action for JP Application No. 2020-517987 dated Jul. 14, 2021 with English translation (10 pages).
International Search Report and Written Opinion for PCT/US2020/038357 dated Sep. 24, 2020 (13 pages).
Notice of Allowance for Korean Application No. 10-2020-7009789 dated Oct. 28, 2021 with English translation (3 pages).
2nd Office Action for Canadian Patent Application No. 3,075,616 dated Jan. 12, 2022 (4 pages).

* cited by examiner

APPARATUSES, SYSTEMS, AND METHODS FOR THE AUTOMATED DISPENSING OF ARTICLES

CROSS-REFERENCE TO RELATED APPLICATIONS

This application is a continuation of and claims priority to U.S. patent application Ser. No. 15/719,671, filed on Sep. 29, 2017, the contents of which are herein incorporated by reference in their entirety.

TECHNOLOGICAL FIELD

Embodiments of the present invention relate generally to automated dispensing of articles, and in particular, to automated dispensing of medications in medication storage units. Embodiments may include full or partial automation of the process and may include mechanisms for improving the efficiency and accuracy of medication dispensing.

BACKGROUND

The dispensing of goods is a common practice that can often be time consuming and prone to error, particularly when performed manually. The automation of dispensing can improve both efficiency and accuracy of the dispensing operation; however, different types of articles necessarily require different types of dispensing. Further, automated dispensing can be costly, and if the dispensing operations are not frequent enough, or there is a low-risk associated with errors, the cost of automation may not be justified.

One particular field in which dispensing accuracy is critical is that of medication dispensing. Medication dispensing, such as in healthcare facilities, can be a complex and time consuming process. With medication orders changing, and with the significant potential ramifications of dispensing the incorrect medication to a patient, the process of delivering medication from the central pharmacy to the patient can be a high-risk process in a healthcare setting.

Healthcare facilities generally dispense medications from a central pharmacy to patients with a number of verification steps performed along the way to ensure that the medication is of the correct type and dose and that the appropriate patient receives the medication. The verification steps may add complexity and time to the process, thereby reducing the efficiency. Therefore it may be desirable to implement apparatuses, systems, and methods which may automate some or all of the process and which may increase the efficiency with which medications are delivered to a patient.

SUMMARY

Embodiments of the present invention may provide an apparatus to facilitate the automated dispensing of articles. Embodiments of the apparatus may include: an end-of-arm tool having a body, two or more vacuum cups extending from the body, where the two or more vacuum cups are movable toward and away from the body of the end-of-arm tool; a vacuum source configured to provide suction to each of the two or more vacuum cups; and a controller, where the controller is configured to cause extension and retraction of each of the two or more vacuum cups independently, and the controller is configured to selectively determine to which vacuum cups suction is applied. The controller may cause the end-of-arm tool to attach to an article using at least one of the two or more vacuum cups. The apparatus of example embodiments may include a valve controlled by the controller, where the valve is used to allow and deny suction to be provided to each of the two or more vacuum cups.

Embodiments may include a vacuum gauge in communication with the controller, where the controller determines that a vacuum cup is attached to an article in response to the vacuum gauge registering a relatively high vacuum reading, and where the controller establishes that a vacuum cup is not attached to an article in response to the vacuum gauge registering a relatively low vacuum reading. The controller may generate an alert in response to determining that a vacuum cup is not attached to an article when it is expected that the vacuum cup is attached to an article. The controller may determine which of the two or more vacuum cups are to be extended based on a size and shape of an article to be retrieved. The controller may provide suction only to the vacuum cups of the two or more vacuum cups that are extended.

According to some embodiments, the controller may determine a level of suction in response to a determined size and weight of the article to be retrieved, and cause the vacuum source to provide the determined level of suction. A size, shape, and weight of the article to be retrieved may be determined based on an identification of the article to be retrieved. The apparatus may optionally include a scanning device configured to scan the article to be retrieved, where the controller determines the identification of the article to be retrieved in response to the scanning device scanning the article to be retrieved. The scanning may include two-dimensional (2D) or three-dimensional (3D) barcode scanning, optical character recognition (OCR), or the like. The identification of the article may include a National Drug Code (NDC) identifier or similar unique identifier that uniquely identifies the type of medication and unit dosage.

Embodiments of the present invention may provide a system for automated dispensing of articles. According to some embodiments, the system may include: a robotic arm; an end-of-arm tool attached to the robotic arm; a scanning device proximate the end-of-arm tool; and a controller to control the robotic arm and the end-of-arm tool. The end-of-arm tool may include a body and two or more vacuum cups extending from the body, where the controller controls a level of suction provided to each of the two or more vacuum cups individually. Each of the two or more vacuum cups extending from the body may be movable between a retracted position proximate the body, and an extended position away from the body of the end-of-arm tool in response to instruction from the controller. Suction may be provided only to the vacuum cups of the two or more vacuum cups that are disposed in the extended position or in the retracted position. Optionally, depending upon package configuration, suction may be provided to a combination of extended and retracted vacuum cups, and possibly not provided to another combination of extended and retracted vacuum cups.

According to some embodiments, the controller may determine which of the two or more vacuum cups to position in the extended position and which of the two or more cups to position in the retracted position in response to determining a size and shape of the article to be retrieved. The controller may determine a level of suction to be provided to the vacuum cups of the two or more vacuum cups in the extended position in response to a determination of the weight of the article to be retrieved. The determination of a size, shape, and weight of the article to be retrieved may be performed in response to the scanning device scanning the article to be retrieved and the controller identifying the article to be retrieved based on the scanning.

Embodiments of the present invention may provide an apparatus including: two or more vacuum cups extending from a body, where each of the two or more vacuum cups may be independently movable between a retracted position relative to the body and an extended position relative to the body; and a controller configured to control the movement of the two or more vacuum cups between the retracted position and the extended position, and to control an amount of suction provided to each vacuum cup independently. The controller may determine which of the two or more vacuum cups to move to the extended position, and which of the two or more vacuum cups to move to the retracted position in response to determining a size and shape of an article to be retrieved. The controller may be configured to determine a location on the article to be retrieved for each of the extended vacuum cups to engage. The controller may control the amount of suction provided to each of the extended vacuum cups in response to determining a weight of the article to be retrieved.

Embodiments of the present invention may provide an automated dispensing system for dispensing articles. An example embodiment may include: a controller configured to receive a request for an article to be dispensed; a first storage module and a second storage module, where each of the first storage module and the second storage module include a plurality of trays movable between a storage position and a retrieval position, where each tray of the plurality of trays may include a plurality of storage locations; a robot configured to access the plurality of storage locations of a tray in response to the tray being moved to the retrieval position; and an end-of-arm tool attached to the robot and configured to retrieve the article from the storage location of the tray in response to a request for said article received at said controller. Systems may include a barcode scanner attached to the end-of-arm tool, where the barcode scanner is configured to scan an identification of the article at the storage location prior to retrieval of said article. The end-of-arm tool may be configured to, with the scanner, scan a unique identifier associated with the storage location of the article. The controller may determine if the unique identifier associated with the storage location is associated with the requested article.

According to some embodiments, each storage module may include a tray elevator, where the tray elevator is configured to move a tray from a retrieval position to an access position, where the access position is closer to the robot than the retrieval position. According to some embodiments, systems may include a refrigerated storage module, where the refrigerated storage module include a plurality of trays, and where each tray of the plurality of trays includes a plurality of storage locations. The refrigerated storage module may include at least one door closure, where the at least one door closure substantially encloses the refrigerated storage module. The at least one door closure may enable one tray of the plurality of trays to be moved from the storage position to a retrieval position while substantially enclosing the remaining plurality of trays in the storage position.

Embodiment of the refrigerated storage module may include a tray elevator, where the tray elevator may be configured to move a tray from a retrieval position to an access position, where the access position is closer to the robot than the retrieval position of the tray, and the at least one door closure may be attached to and move with the tray elevator. Embodiments may include a memory, where the memory may be configured to store a unique identification for each of the plurality of locations for each of the plurality of trays, and an identification of an article stored in each of the plurality of storage locations. Embodiments may optionally include a track system, where the robot may advance along the track system between the first storage module and the second storage module.

Embodiments may provide a method of operating an automated dispensing system. Methods may include: providing for storage of a plurality of trays in a vertical stack in a storage module, where each tray is individually movable between a storage position and a retrieval position, and where each tray may include a plurality of uniquely identified storage locations, and articles disposed in the uniquely identified storage locations; receiving a request for a first article at a controller; causing a tray including a unique storage location having therein the first article to be moved from the storage position to the retrieval position; commanding a robot to retrieve the article from the unique storage location; and dispensing the article to a dispensing location. Commanding the robot to retrieve the article may include commanding the robot, using an end-of-arm tool, to attach to the first article and to remove the first article from the unique storage location.

According to some embodiments, methods may include reading an identification of the unique storage location prior to retrieving the first article using at least one of a barcode scanner or a radio frequency identification reader attached to the end-of-arm tool. Methods may optionally include: reading an identification of an article using the at least one barcode scanner or radio frequency identification reader attached to the end-of-arm tool; and dispensing the first article to the dispensing location in response to the identification of the article corresponding to the request. Methods may include causing the tray including the unique storage location to be moved from the retrieval position to an access position by a tray elevator.

Embodiments of the present invention may provide an automated dispensing system including: a controller configured to receive a request for an article to be dispensed; a storage module, where the storage module includes a plurality of trays movable between a storage position and a retrieval position, where each tray of the plurality of trays include a plurality of storage locations; a tray elevator configured to move a tray from a retrieval position to an access position; a robot configured to access the plurality of storage locations of a tray in response to the tray being moved to the access position, where the access position is closer to the robot than the retrieval position; and an end-of-arm tool attached to the robot and configured to retrieve the article from a storage location of the tray in response to a request for said article to be received at said controller.

According to some embodiments, the end-of-arm tool may include at least one of a barcode scanner or a radio frequency identification reader, and where the at least one of a barcode scanner or a radio frequency identification reader is configured to read an identifier of said article prior to retrieval of said article. The automated dispensing system of example embodiments may include an end-of-arm tool having: an end-of-arm tool body; two or more vacuum cups extending from the body, where the two or more vacuum cups are movable toward and away from the body of the end-of-arm tool; and a vacuum source to provide suction to each of the two or more vacuum cups. According to some embodiments, the controller may be configured to cause each of the two or more vacuum cups to extend and retract independently, and where the controller may be configured to selectively determine to which vacuum cups suction is provided.

DESCRIPTION OF THE DRAWINGS

Reference now will be made to the accompanying drawings, which are not necessarily drawn to scale, and wherein.

DETAILED DESCRIPTION

Figure 1:
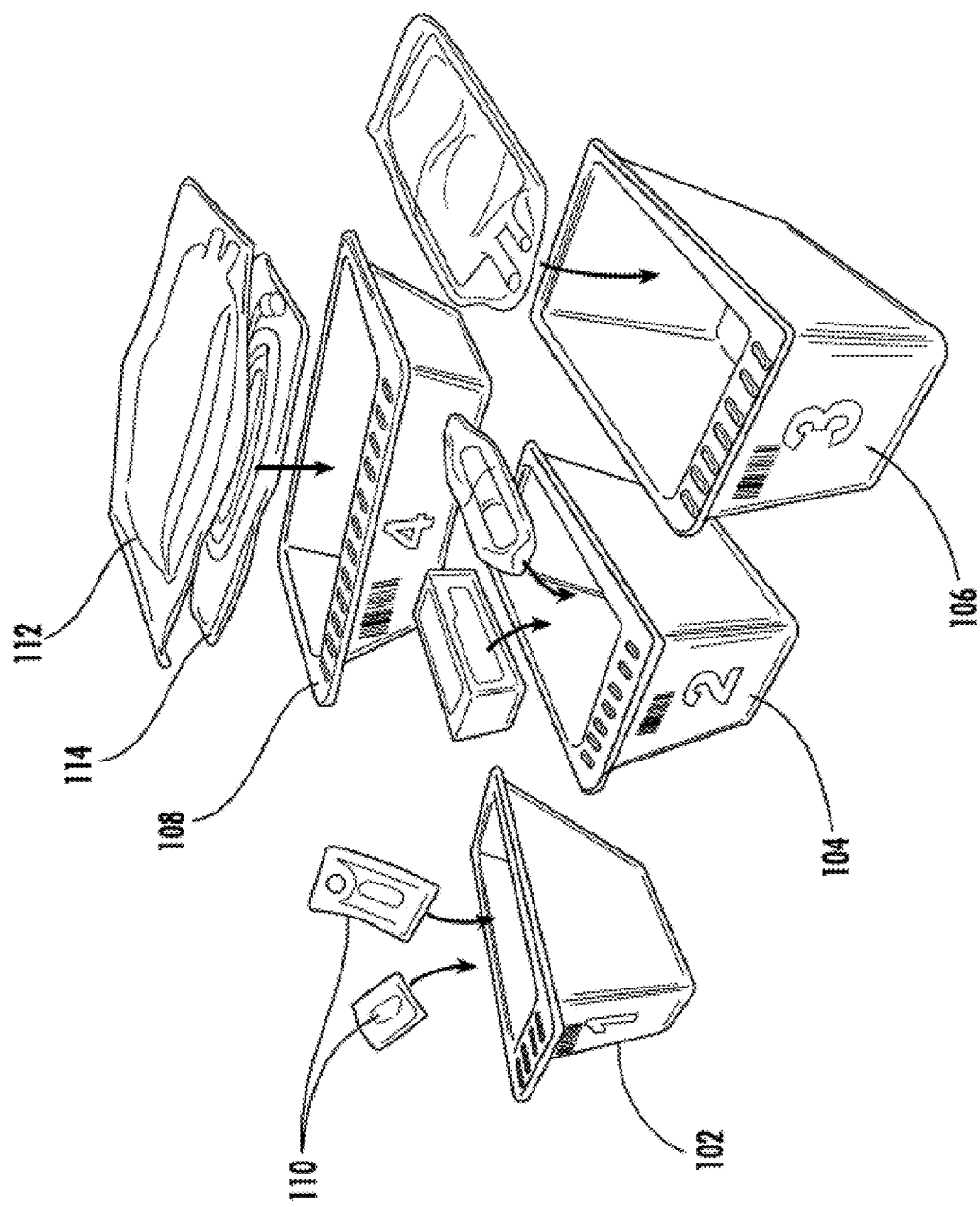
FIG. 1 illustrates an example embodiment of overpacks as described herein using multiple sized bins of a common profile.

Embodiments of the present invention may provide various apparatuses, systems, and methods for improving the efficiency of medication distribution within a healthcare facility. Some embodiments and components of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements.

Example embodiments of the present invention may provide a method, apparatus, and computer program product which may facilitate the automated dispensing of articles, such as the dispensing of medications within a healthcare facility. Embodiments may improve the efficiency and accuracy of dispensing articles, incorporating mechanisms that may solve issues identified by the applicant as substantial hurdles in automating the dispensing of articles, particularly when those articles are of differing sizes, shapes, and weights.

While embodiments of the present invention may be described primarily with respect to the dispensing of medications and medical supplies in healthcare facilities, such as hospitals and long-term care facilities, for example, embodiments of the inventions described herein may be implemented in a variety of types of facilities, not limited to those explicitly described herein. For example, embodiments may be implemented in distribution warehouse environments in which articles may be dispensed for fulfilling orders. While certain aspects of embodiments described herein may be specific to medication dispensing and the associated accuracy required therewith, similar implementations may omit certain features or include other features as would be apparent to one of ordinary skill in the art.

Healthcare facilities may include a central pharmacy in which medications are stored and dispensed to areas throughout the healthcare facility. Some healthcare facilities may rely on a supplier, distribution center, or remote central pharmacy which stores medications and supplies at a remote location and delivers the medications and supplies on an as needed basis. In such an embodiment, the medications from the supplier, distribution center, or remote central pharmacy may be received by a healthcare facility at a receiving area. While embodiments of the present invention may be described as dispensing medication from a central pharmacy, embodiments in which central pharmacies are located remotely or embodiments using distribution centers may implement embodiments of the inventions from the area in which medications and supplies are received from the central pharmacy or distribution center. The indication of medications needed may be provided to the central pharmacy or distribution center with sufficient lead time such that the healthcare facility may receive the medications in advance of when they are needed.

Articles to be Dispensed

While automated dispensing systems of example embodiments described herein may be used to dispense various types of articles, the primary embodiment described herein is particularly well suited for dispensing medications. The modularity and storage module types may be configured to accommodate the needs of any form of medicinal storage or medical supply storage. However, it is appreciated that other articles may similarly benefit from the various, configurable storage modules described herein for automated dispensing systems.

As noted above, an automated dispensing system according to example embodiments may be implemented in, for example, a central pharmacy of a healthcare facility. Medications dispensed from a central pharmacy may be of a variety of form factors from individual pills or capsules to intravenous bags of a liter or more capacity. Other form factors may include syringes, carpujects, vials, multi-dose medication containers, etc. Supplies, such as intravenous medication tubing, empty syringes, etc. may be dispensed from a separate medical supply distribution center within a healthcare facility, or in some cases, the central pharmacy and medical supply distribution operations may be combined. Both the supplies and the medications may come in a variety of sizes and shapes and may not easily and efficiently dispensed from a conventional automated dispensing apparatus. While a unit dose medication contained in a blister package may be easily handled due to the small size and a substantially planar surface available for vacuum cup retrieval as described further below, intravenous bags may be relatively cumbersome with non-rigid packaging and a relatively high weight. Further, the handling of products may require different levels of care. For example, a carpuject, ampoule, or a vial may be relatively fragile while a unit dose of a medication, such as a tablet, may be relatively durable. While the tablet may be stored and dispensed in a very small package without substantial protection from transport, the vials, carpujects, and ampoule may require larger, more durable packaging. Similarly, intravenous medication bags may be durable for transport, but may be easily punctured such that care must be taken in storing, handling, and distributing such products.

While certain medications are configured to be dispensed in vials where a syringe is a required supply to accompany the vial, other medications may require a patient to consume food or a beverage other than water. In such cases, the food or beverage to accompany the medication may be treated as a supply, and such supplies may also be dispensed as other supplies may be dispensed as described herein.

According to some embodiments described herein, some products may be repackaged into overpacks or packaging that encases or holds the medication or supplies in a package form factor that is one or more of more uniform, more easily grasped, more easily stored, etc. Overpacks may provide a common packaging size, profile, shape, grasping feature, content protection, etc.

Provided herein are various embodiments of uniform or quasi-uniform overpacks or secondary packaging for use with a variety of medications and supplies with varying shapes, sizes, and handling requirements (e.g., fragile, temperature sensitive, etc.). The overpacks described herein may provide an aspect of uniformity to generally non-uniform form factors. The uniformity may be in the profile of the overpack, such as when the overpack includes a plurality of various sized bins with uniform profiles, or the uniformity may be in a locating/holding hole of a plurality of various sized bags configured to hold the various form factors.

FIG. 1 illustrates an example embodiment of an overpack according to example embodiment of the present invention using bins of varying sizes with a common profile. Each of the illustrated bins 102, 104, 106, and 108 are of a different size while maintaining a common profile. The smallest bin 102 may be configured to hold small items such as unit doses of oral medication 110 (e.g., pills, capsules, tablets, etc.) while the largest bin 108 may be configured to hold large items such as a one liter intravenous bag 112 and/or intravenous tubing 114, each of which may be too large to fit into any of the smaller bins 102, 104, or 106. The bins between the largest and the smallest (bins 104, 106) may be appropriately sized to hold medications and/or supplies such as vials, syringes, 100 mL intravenous bags, or the like. The uniform profiles of the bins may allow the bins to be processed along a conveyor line configured to accommodate such a profile. Further, the uniform profile bins may be stored on common shelves with only the width of the shelf occupied varying between bins of different sizes. While some embodiments of bins of varying size may include a variable length, other embodiments may include a common length and a variable depth. For example, each bin may occupy the same width of a shelf, but the bin may extend further back on the shelf to create added capacity.

In some example embodiments, the overpacks may be sealed or closed to keep the contents of the overpack protected and/or secure. For example, the various sized bins of FIG. 1 may include lids which may be secured to the bins by a hook-and-loop fastener system, a snap-on lid, or a heat or ultrasonically welded plastic film seal. The type of closure used for the overpack may be dependent upon the use of the overpack. For example, an overpack for manual distribution (e.g., via a nurse cart) within a healthcare facility may not require a closure, or may use a simple snap-on closure. An overpack for automated distribution within a healthcare facility, or an overpack for distribution through an over-the-road delivery service may require a more secure closure that is less likely to be inadvertently opened, such as a heat-sealed film closure.

The closure may also depend upon the type of contents contained within the overpack. For example, if the overpack contains environmentally sensitive contents that should not be exposed to humidity or moisture may benefit from a heat-sealed film closure. Closures that are impervious to air and moisture may also be used for overpacks used with oxygen sensitive contents where an inert gas fills the overpack.

Figure 2:
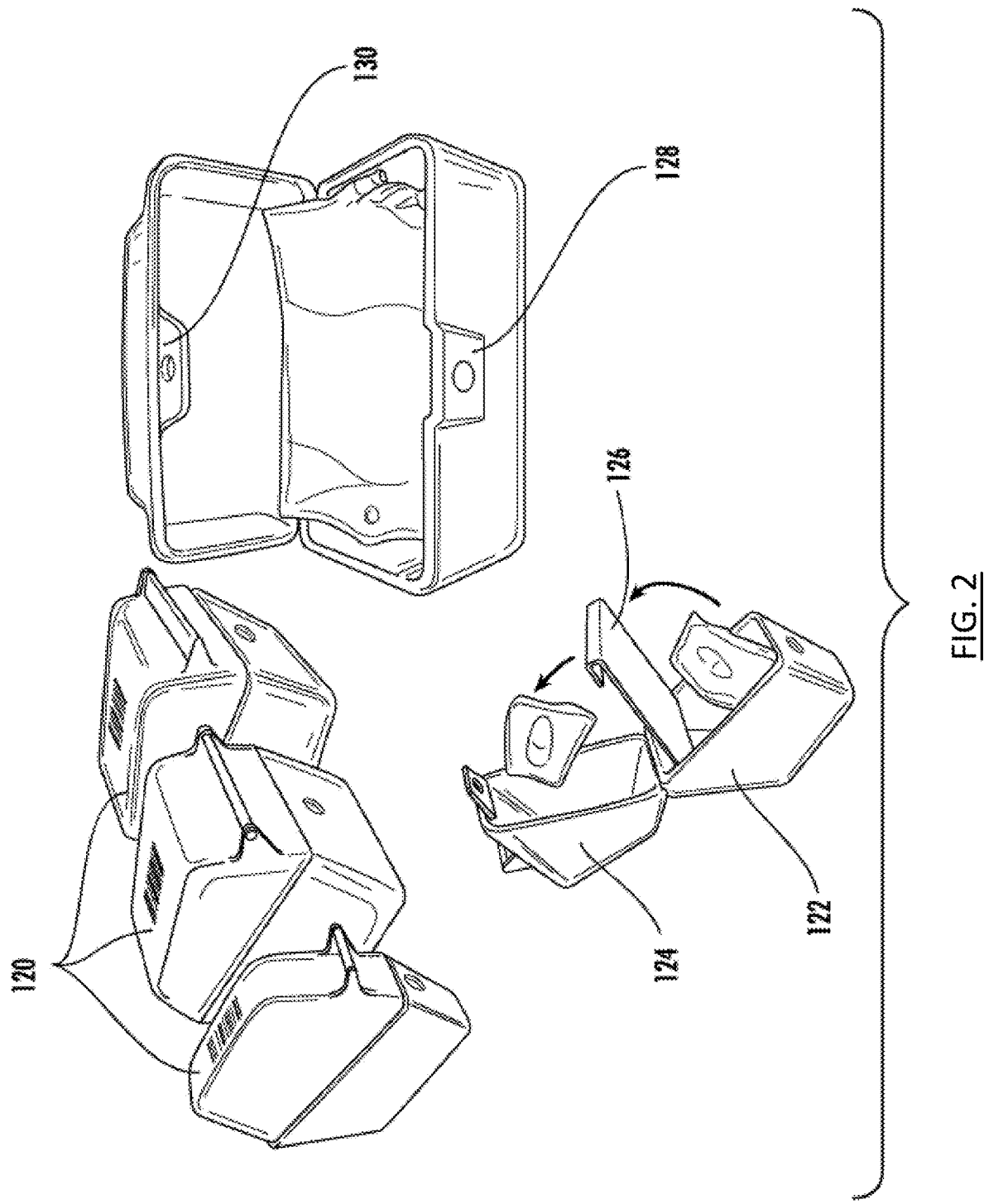
FIG. 2 illustrates another example embodiment of overpacks including lidded containers of multiple sizes, each having a common profile.

A closure for an overpack may also be selected based upon whether the contents are government regulated, as in the case of controlled substances, or if the contents are a high-value candidate for theft. In such embodiments, a lockable closure may be used to seal the overpack. FIG. 2 illustrates an example embodiment of an overpack with a hinged closure. As illustrated, the overpacks 120 of FIG. 2 may include a common profile, but have varying widths to accommodate medications and supplies of various sizes. The overpack base 122 and hinged lid 124 may open in a clamshell fashion to allow access to the interior cavity containing the medication or supply. As shown, the overpack may include a divider 126 which may allow two articles to be carried within one overpack without the two interfering with one another. The separation afforded by the divider may help to reduce confusion or mistakes when multiple medications are contained in an overpack for a particular patient. Also illustrated in the overpacks of FIG. 2 are a closure mechanism including a tab 130 received within latch 128. The closure mechanism may be a locking mechanism requiring a key, code, or biometric identifier. For example, authorized medical personnel may have access to a key, such as a magnetic key kept on their person or at a nurse station, which may unlock the latch 128. Optionally, the latch may be a push-button release configured only to maintain the lid 124 in a closed position during transport.

While closures and locks may be used to secure controlled substances, security of controlled substances may additionally rely upon security by obscurity, in which narcotics and other controlled substances are not distinguished from non-controlled substances, such that locating controlled substances among the plurality of medication overpacks may be difficult. Further, as described below, the storage location may comprise the security measures necessary to secure narcotics or high-value articles such that overpacks, if used, may not require any additional security measures.

Figure 3:
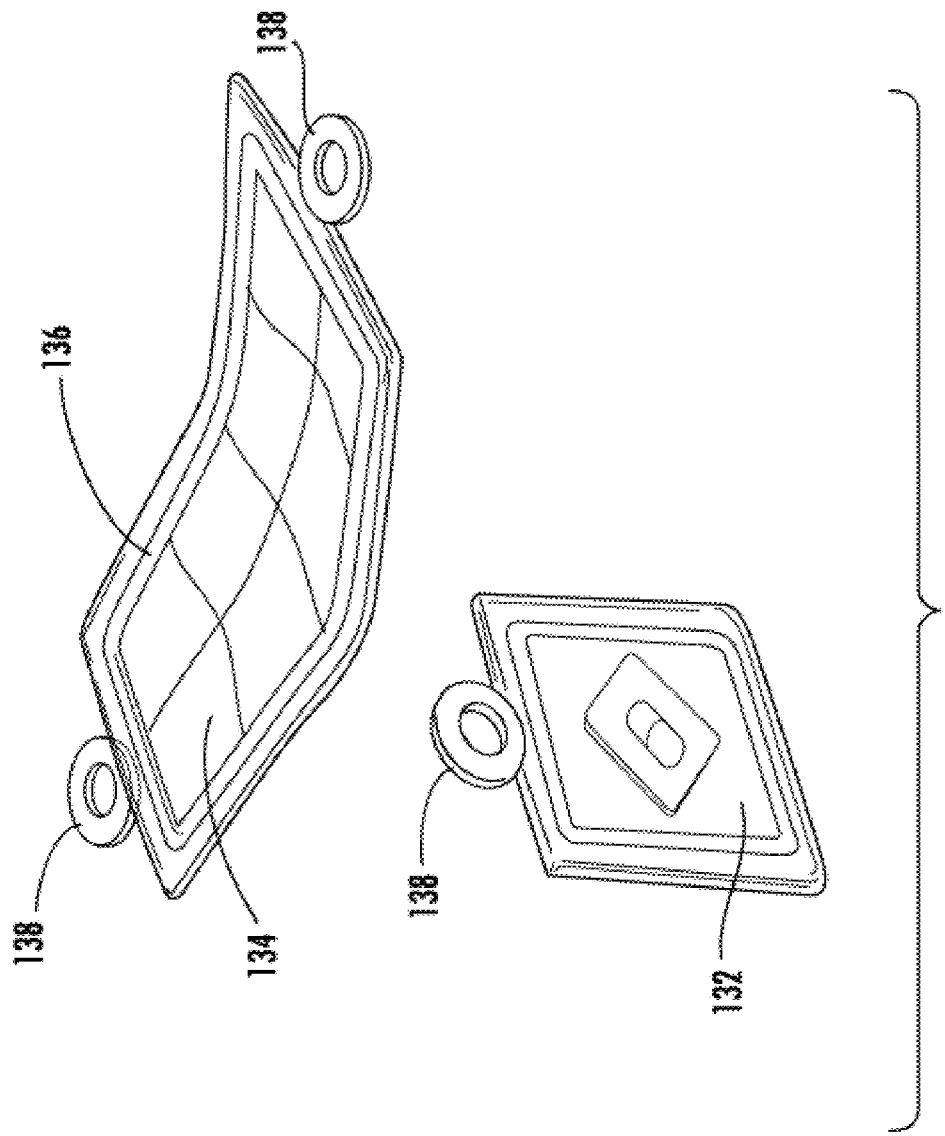
FIG. 3 illustrates another example embodiment of an overpack including a flexible film pouch with a grasping loop.

FIG. 3 illustrates another example embodiment of an overpack. The illustrated embodiment of FIG. 3 is a reusable folding pouch style overpack which may be available in various sizes to accommodate multiple sizes of medications and supplies. The pouch 132 may be made of a pliable material 134 which may be elastic to better hold the contents without shifting. The material may also be substantially transparent to allow easy verification of the contents of the pouch. The material 134 may have an adhesive strip 136 around the perimeter such that when the sheet of material 134 is folded, a pouch 132 is formed. The adhesive strip 136 may be a hook-and-loop type fastener or a releasable adhesive material to allow the pouch to be easily opened and reclosed for re-use. Optionally, the pouch style overpack may be designed for a single-use and may include a non-releasable adhesive requiring the pouch 132 to be torn open. Such a single-use type pouch may be beneficial for embodiments requiring evidence of tampering. The pouch 132 may also include a loop 138 or hook which may be used to hang or grasp the pouch in transport and dispensing. As outlined above, some overpacks may include a common sized and/or shaped grasping feature, such as the loop 138 to aid automation or efficient handling as opposed to, or in combination with, a common size or profile.

Figure 4:
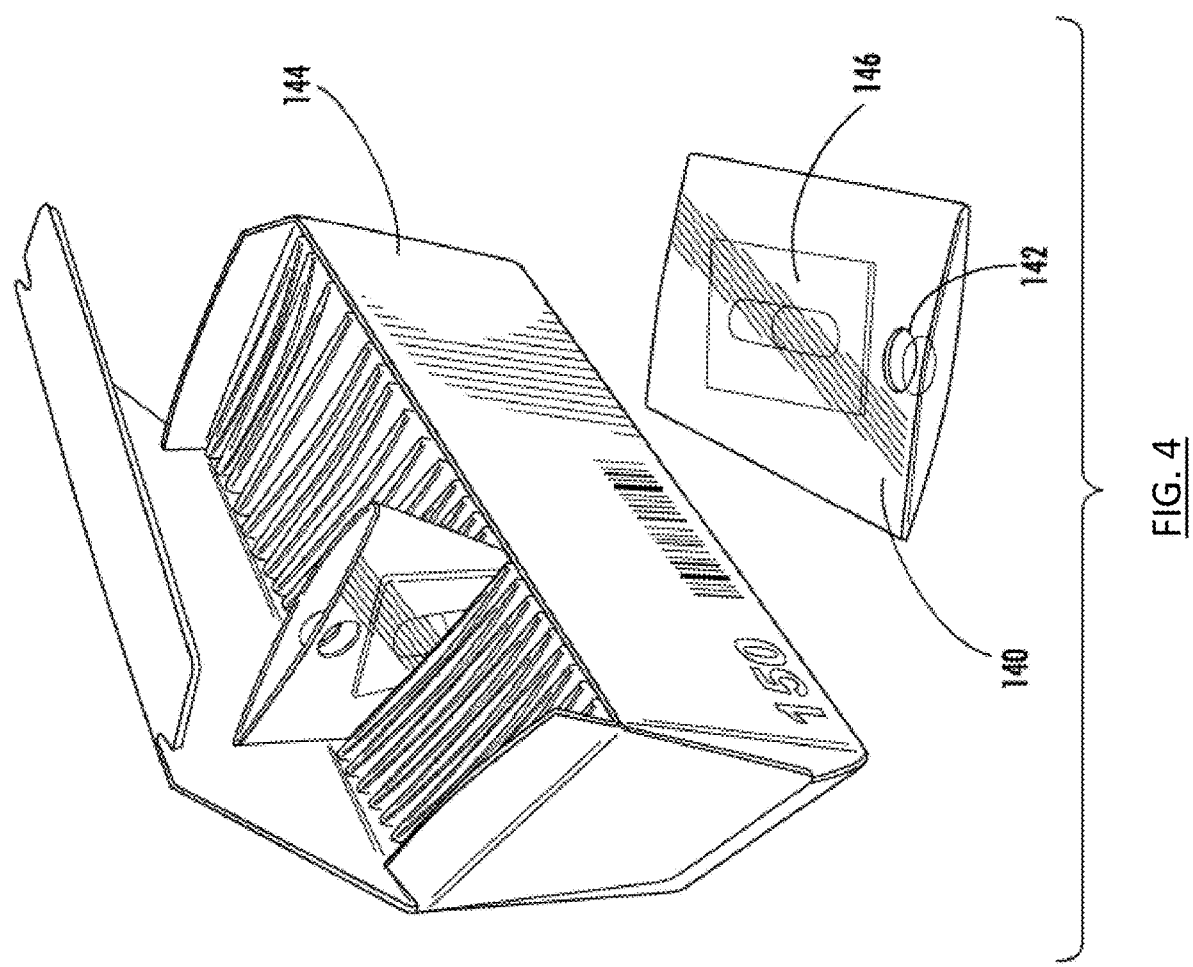
FIG. 4 illustrates an example embodiment of bags used as an overpack.

Overpacks according to the present invention may be embodied in other forms, such as envelopes or bags. FIG. 4 illustrates an example embodiment of an overpack in the form of a bag 140 including a hole 142. The bag type of overpack may be of any necessary size to accommodate the medication or supplies carried therein, and the hole 142 may be used for holding, storing, and grasping the bag 140. The bag or envelope style overpack may be conducive to use in instances where the medication or supply is received from a supplier as the cost of the overpack and material used therein is relatively minimal. Further, pharmacy automation tools, such as an automated dispensing system, may be configured to package and dispense medications and supplies in such overpacks, such that manual packaging of the medications or supplies into overpacks may not be required, thereby increasing efficiency and reducing cost. Some medications may be available from a supplier in bulk quantities in such overpacks, such as the illustrated box 144 of unit dose blisters 146 supplied in bag style overpacks 140.

Figure 5:
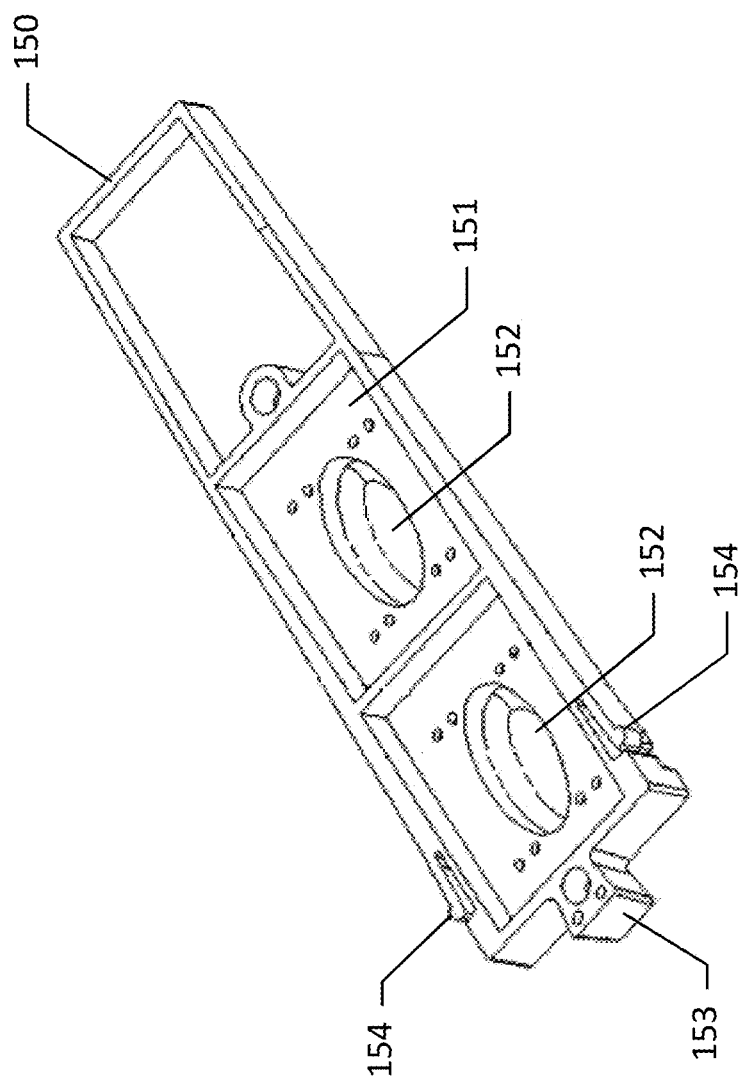
FIG. 5 illustrates a unit dose carrier defining a plurality of cavities therein.

Unit dose blisters may be cumbersome or somewhat challenging for automated handling due to their irregular sizes and shapes. However, example embodiments described herein may provide a mechanism for ease of storage, retrieval, and identification of blister packs. FIG. 5 illustrates a unit dose carrier 150 defining a plurality of cavities 151 therein. Each cavity may be configured to receive a unit dose of medication of a unit dose blister. The cavities 151 may include recesses 152 sized to receive the medication blister extending from the backing of a medication unit dose blister pack (i.e., the protrusion containing the actual medication unit dose). This enables a medication unit dose blister pack to be received within the cavity with the blister pack backing facing up as the blister pack backing generally contains information identifying the medication on the side opposite the blister, which is received within recess 152.

The size, shape, and depth of the cavities 151 and recesses 152 may be configured to accommodate a large sampling of unit dose blisters of various shapes and sizes. According to the carrier 150 of FIG. 5, the carrier is configured to hold two unit dose blisters, with one in each cavity 151. As shown, a unit dose blister is able to be received within each cavity 151 with the medication blister facing down and received into recess 152. This orientation will position the unit dose blister to lie substantially flat in a plane defined by the carrier 150, leaving the identification information and other printed medication information (e.g., the information displayed on the side of the blister backing opposite the blister) viewable from above the carrier. This enables scanning of information regarding the medication unit doses contained within the carrier 150.

Beyond the uniform orientation of medication unit doses to be readily identified in the carrier 150, the carrier configuration allows a reliable mechanism for a picking system to vacuum pick (e.g., using a blister removal mechanism) the unit dose blister during a retrieval and delivery process. The carrier of FIG. 5 further includes a tab 153 that may enable an automated picking system to retrieve the carrier 150 and to transport carrier using the tab 153 as a location to grab. Further, the illustrated carrier 150 includes retainers 154 which may be configured to retain the carrier 150 inside a housing, such as a housing carrying a plurality of carriers. This may preclude inadvertent movement of the carrier from the housing which may be caused, for example by system vibrations.

Figure 6:
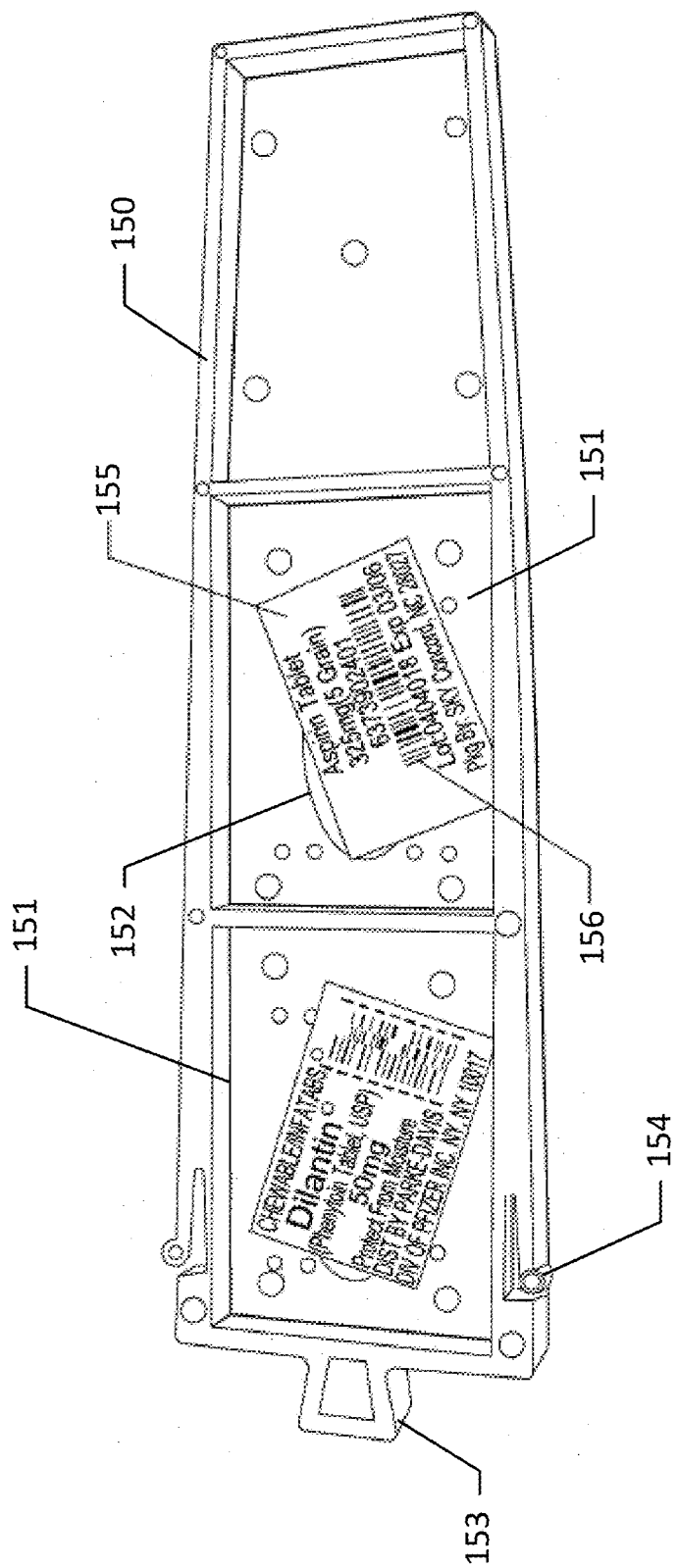
FIG. 6 illustrates another view of the carrier of FIG. 5 including two unit dose blister packs received within the cavities.

FIG. 6 illustrates another view of the carrier 150 including two unit dose blister packs received within the cavities 151. As shown, the blisters of the blister packs are facing down, with the blisters received within recesses 152. The identifying information regarding the medications of the unit dose blister packs is visible on the planar surfaces facing up, such as the name of the medication 155 and a machine readable barcode 156. Further, the substantially planar backing to the blister packs provides a smooth surface that can be engaged by a vacuum picking device using a suction cup type retrieval tool. This enables each medication unit dose blister to be individually picked from the carrier 150 without disturbing the remaining medication unit dose blisters.

Figure 7:
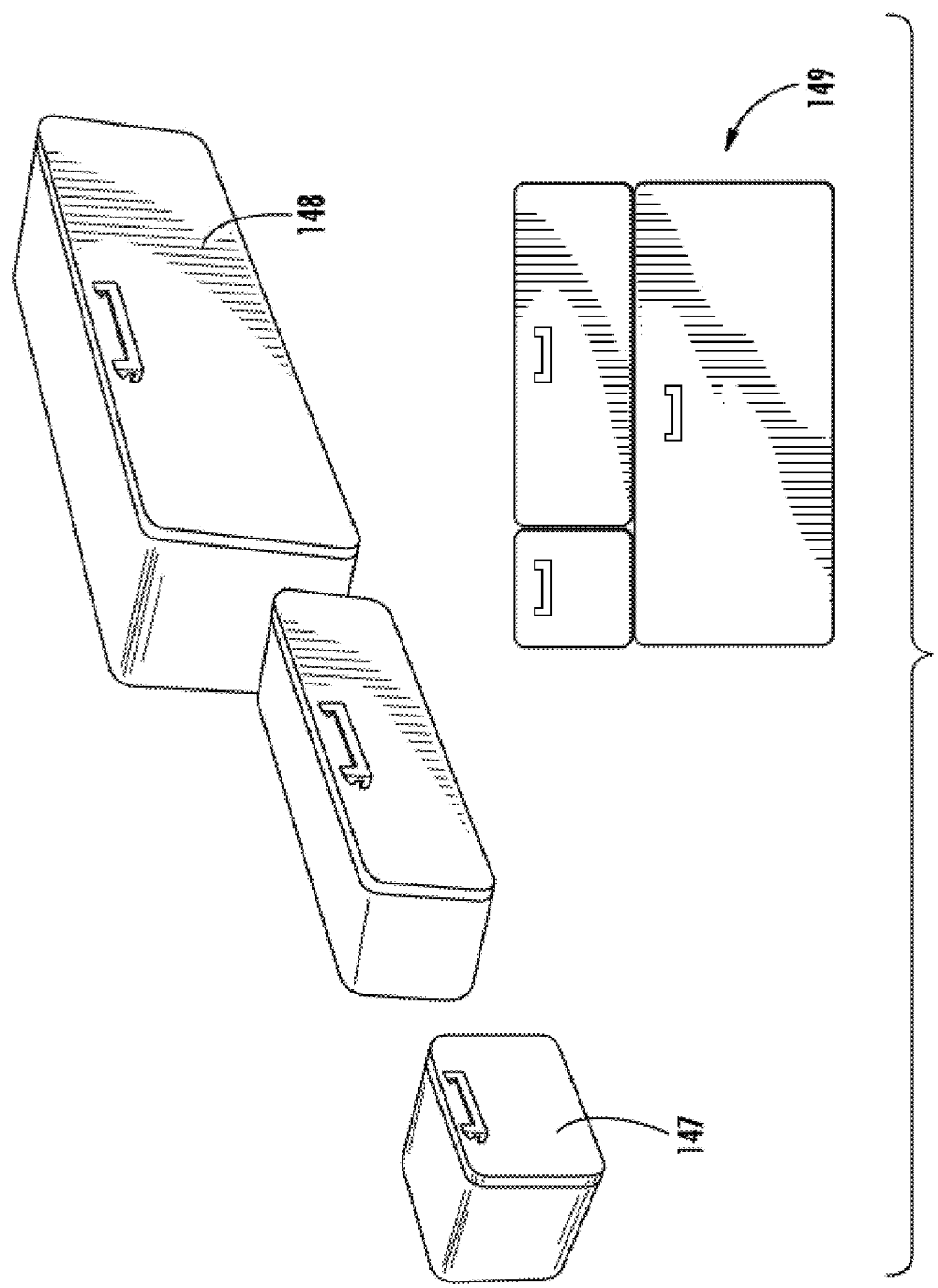
FIG. 7 illustrates multiple sized boxes as overpacks.

FIG. 7 illustrates another example embodiment of overpacks according to embodiments of the present invention.

The illustrated embodiment includes various sizes of boxes, ranging from a small box 147 to a large box 148. The small size and the large size may be dictated by the sizes of medications and supplies to be handled within a healthcare facility. In the illustrated embodiment, the boxes 147, 148 include hinged doors on a front side of the box. The doors may be hinged proximate the bottom of the front, opening outward. The boxes may include a common depth such that the boxes may be arranged in a stacked configuration 149 while each of the doors to each of the boxes remain accessible.

Figure 8:
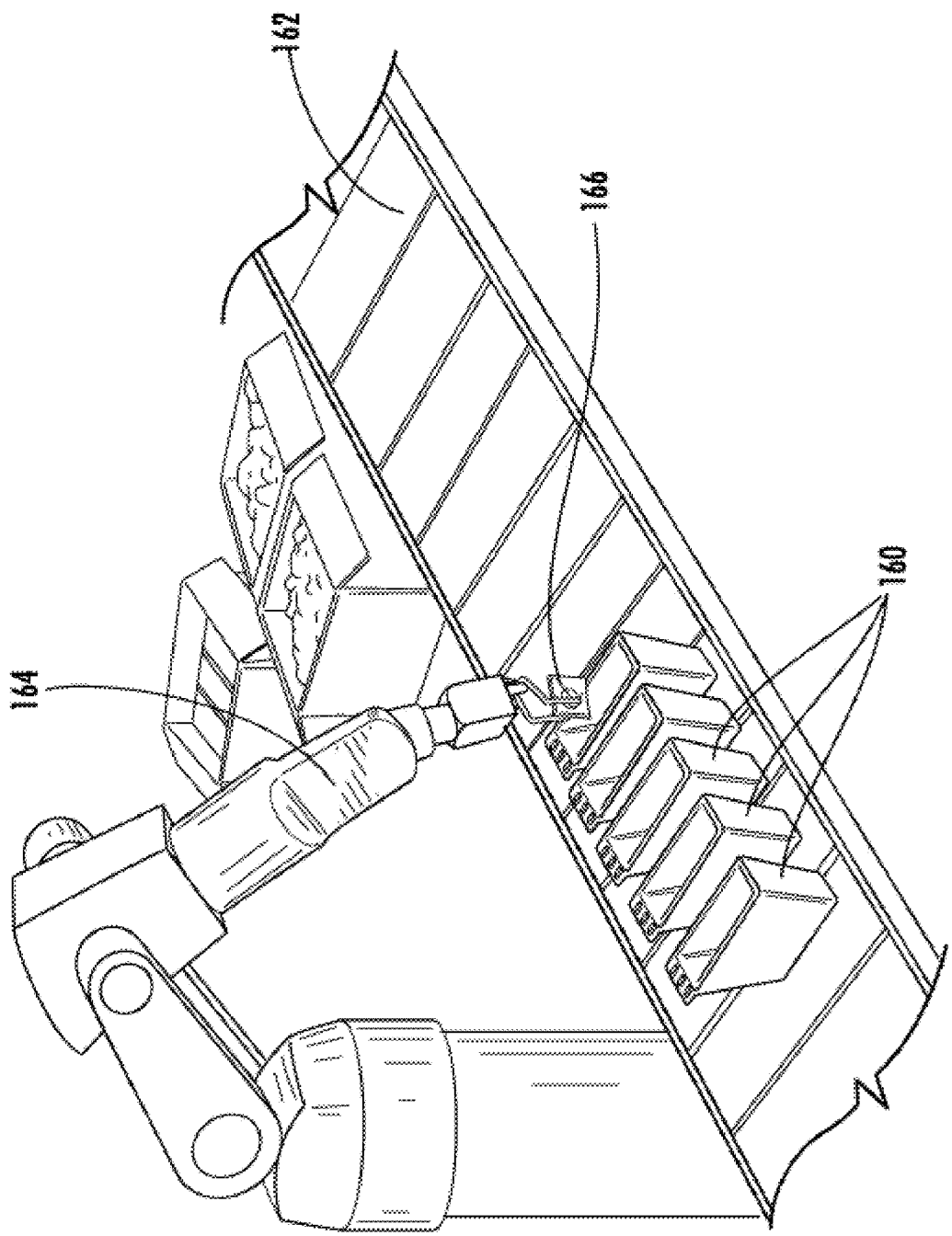
FIG. 8 illustrates automated loading of overpacks according to an example embodiment of the present invention.

While some overpacks described above may be used for storage of a medication or supply in an automated dispensing system, such as in a central pharmacy, other overpacks may be used for receiving medications or supplies once dispensed from the automated dispensing device. For example, overpacks according to embodiments of the present invention may also facilitate automation of medication order fulfillment. For example, as illustrated in FIG. 8, empty bins 160 of various sizes but of a common profile may be configured to be transported along a conveyor 162 and be filled by a robot 164 or other form of automation. The robot 164 may place a medication or supply 166 into the bin 160 for dispensing to a patient. Embodiments of the present invention may also be used with existing automated pharmacy dispensing systems which may distribute medications from an inventory to an overpack for transport to a location proximate a patient. Thus, medication overpacks may be implemented for storage within an automated dispensing device as described further below, and/or implemented for receiving the dispensed medication. According to some embodiments, an overpack used within an automated dispensing device, such as the overpack 140 of FIG. 4, may be dispensed by the automated dispensing apparatus to another overpack, such as the bins of FIG. 1 as illustrated in FIG. 8.

Overpacks may be configured to contain only a single medication (i.e., a unit dose), a medication and a related supply (e.g., a vial of medication and a syringe), or the overpacks may be configured to contain multiple medications destined for the same patient. For example, if a patient requires five medications in the morning, three in the middle of the day, and four medications in the evening, an overpack may be filled with the five morning medications, a second overpack may be filled with the three middle-of-the-day medications, and another overpack may be filled with the four evening medications. In such an embodiment, individual tracking and control over unit dose medications may be lost; however efficiencies may be gained by using only a single overpack for each time of day that medication is required for the patient.

As described further below, systems of example embodiments may include a bagging station where one or more medications are placed into a bag and the bag becomes the overpack. In such an embodiment, medications may initially be retrieved and dispensed to a bin, where the bin is taken to a bagging or bag-loading device. The bags at the bagging station may be in a web of bags (e.g., on a roll or spool of bags) where the bags are either predefined lengths separated by perforations and sealed at one end, or the web of bags may be a continuous web of a tube of material, where the bagging station may seal the bags at one or both ends, and separate bags from one another as needed.

According to some embodiments, at a bagging station, a bag is printed to, with information such as the contents to be placed into the bag, a destination for the bag, a patient to whom the contents of the bag are prescribed, or the like. The bag may be printed with a unique, machine readable identifier for ease of machine recognition. The bag may be indexed to a position, scanned to ensure the indicia printed to the bag is appropriate, and then opened to receive medications.

Figure 9:
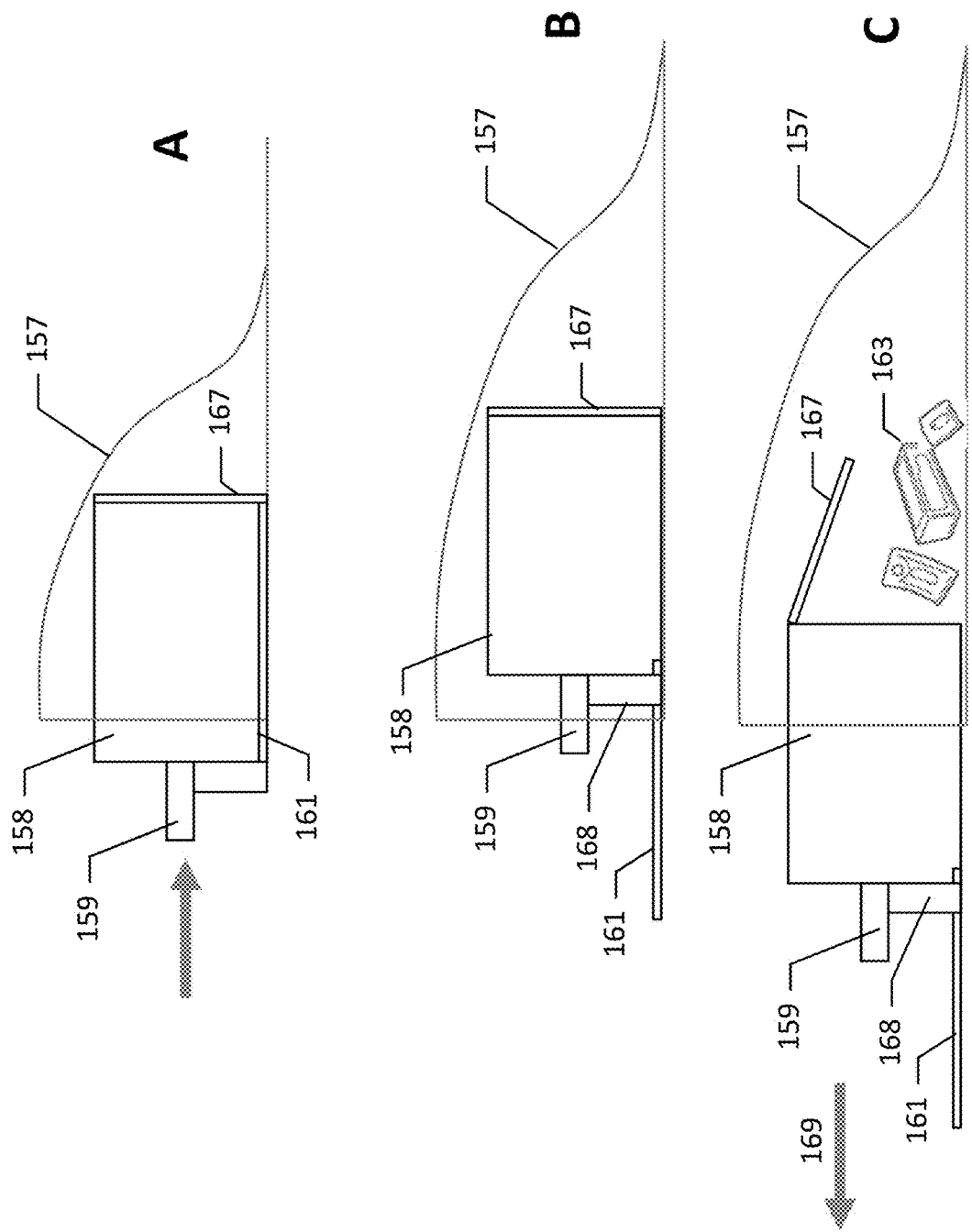
FIG. 9 illustrates an example embodiment of a bag loading operation at a bagging station.

FIG. 9 illustrates an example embodiment of a bag loading operation at a bagging station. As shown at A, loading bin 158 containing one or more medications is inserted into an open bag 157 at the bagging station. The loading bin 158 may be advanced, for example, by the robot 204 using an end-of-arm tool at 159. The loading bin includes a floor 161 and an end panel 167. As shown at FIG. 9B, once the loading bin 158 is inserted into the bag 157, the floor 161 is retracted, which may be enabled by a variety of mechanisms, such as a gear drive 168. Sliding the floor 161 from under the bottom of bin 158 leaves the contents of the bin inside the bag 157. As shown at C, the end panel 167 is raised, thereby allowing the bin 158 to be withdrawn from the bag along arrow 169. The medications 163 are thus deposited within the bag 157 with minimal risk of damaging any of the medications.

The bags of example embodiments may have resealable features which may be sealed and resealed upon removal of one or more articles. For certain medications or facilities, a tamper-evident seal may be more desirable. As noted above, the bags may be formed from a continuous web and may be filled without being separated, such that a bandolier of bags may be formed, which may be useful in embodiments in which multiple bags are destined for the same location or prescribed to the same patient. Optionally, medications may be dispensed for restocking medication cabinets, such that a bandolier of bags may be useful for restocking different medications within the same cabinet. Bags may be equipped with holes to minimize trapped air within the bag, and may include quick-access perforations to allow the bag to be easily opened. The printed portion or a portion thereof of the bag may be attached via perforation for easy removal. Patient information or information protected under the Health Information Protection Act (HIPAA) may be removable from the bag to comply with such protections. Bags may optionally be opaque or translucent rather than transparent to protect patient privacy or to mask the type of medication, such as narcotics, which may be a desirable target for theft.

According to some embodiments of the present invention, overpacks may also include identifying indicia disposed thereon for identifying the contents of the overpacks. In one embodiment, the overpacks may include an overpack identification number which is correlated with a medication or supply that is placed into the overpack. The correlation between the overpack identification number and the contents may be performed by an automated system that loads the overpacks. Such a correlation would allow an overpack to be scanned to determine the overpack identification number, and then referenced in a database to determine the contents of the overpack without requiring a person to review the contents of the overpack. The database may be maintained by a server in the healthcare facility configured to track and monitor medication dispensing within the healthcare facility.

Figure 10:
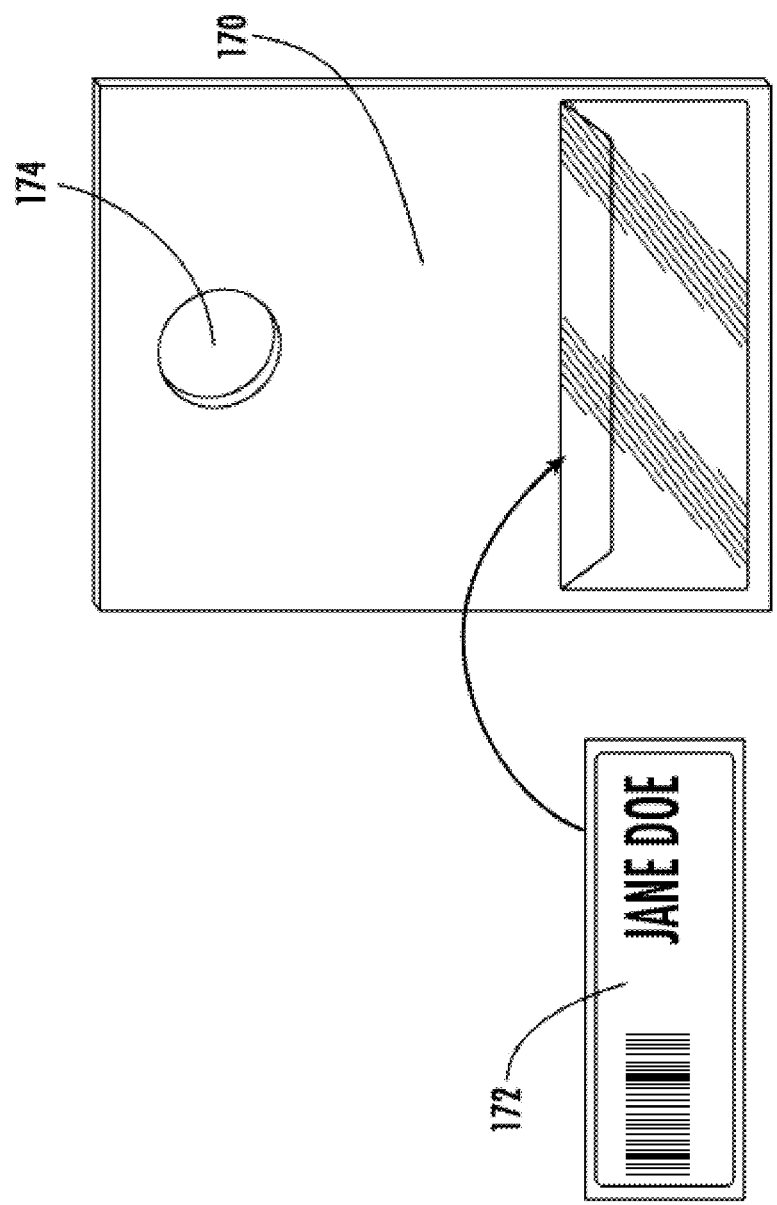
FIG. 10 illustrates another example embodiment of an overpack including a card-stock backing.

According to another embodiment, the overpack may include a label that is written to for denoting the contents of the overpack. FIG. 10 illustrates an example embodiment of a patient identification label 172 that is printed and paced into an overpack 170. The illustrated overpack may be a blister pack, bag, or envelope configured to receive a medication unit dose. The overpack 170 may further be configured with a hole 174 for uniform storage and retrieval. While illustrated as a patient identification label 172, the label attached to an overpack may identify the contents of the overpack without regard for a specific patient. In the illustrated embodiment, the patient identification label may include a barcode or other indicia identifying the patient and the patient identification label 172 may be inserted into a pocket or otherwise affixed to the overpack 170. The identification may also be printed directly onto the overpack material rather than onto a separate label.

Figure 11:
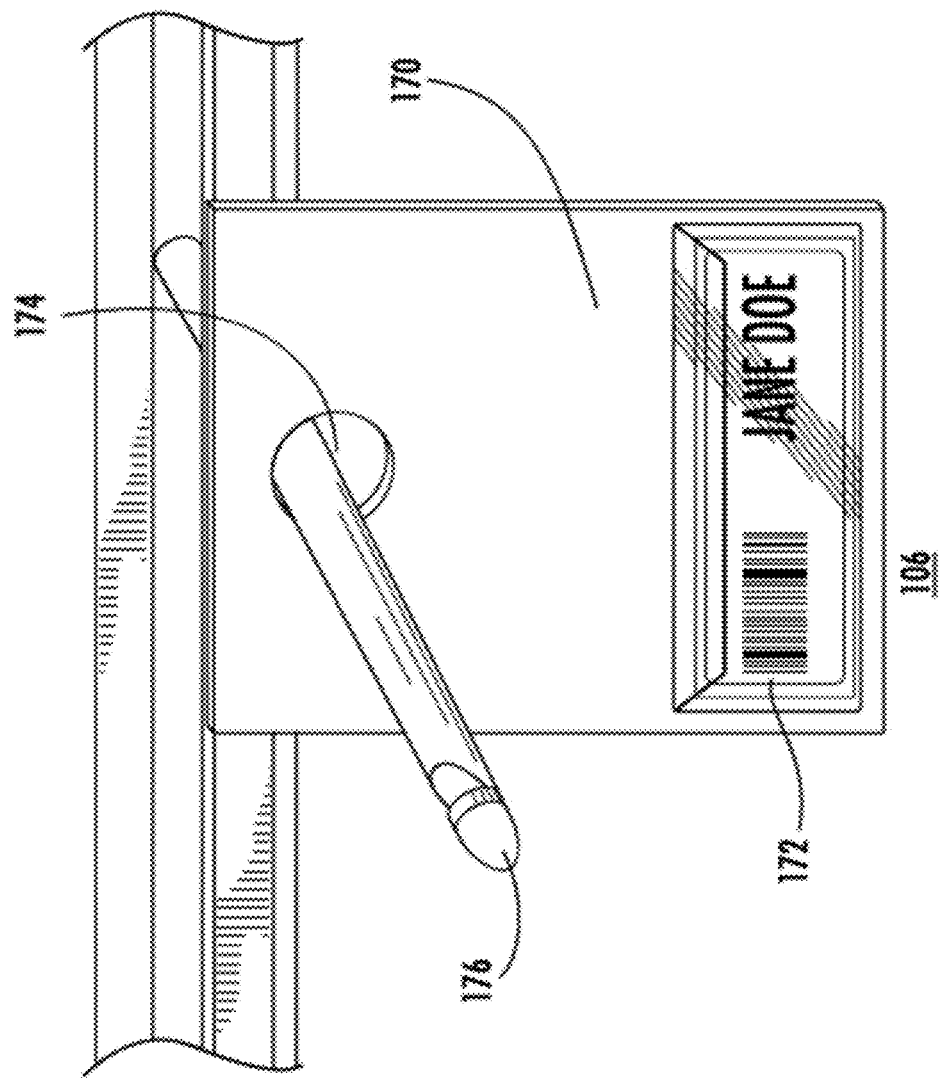
FIG. 11 illustrates the storage of overpacks according to an example embodiment of the present invention.

FIG. 11 illustrates an example embodiment of the overpack 170 as carried on a rod 176. The overpack 170 may be carried on the rod 176 for automated distribution, transport, or storage. While the illustrated patient identification label 172 includes a barcode and name, embodiments may include a patient or overpack contents label that includes a radio frequency identification (RFID) label configured to be read by an RFID reader exclusive of or in addition to other identifying indicia, which may include barcodes, text, or other human or machine readable information. In some embodiments, the label 172 may include an image of the medication that is supposed to be contained within the overpack 170 to allow authorized medical personnel to visually confirm the contents of the overpack are correct. While identifying indicia may be printed to a label, embodiments of the present invention may include overpacks using electronic ink labels. Electronic ink labels may be "printed" by programming such that when a medication or supply is loaded into an overpack the electronic ink label is programmed to display identifying indicia about the medication or supply contained within the overpack. Electronic ink labels may function in the same manner as conventionally printed labels (e.g. by thermal printing, ink jet printing, laser printing, etc.) such that they may be read by a user or by a reading device.

Additionally or alternatively, medications, such as blister packs may include identifying information printed to the blister pack. Overpacks may be configured such that the identifying indicia of the medication packaging is readable through the overpack. For example, a blister pack with identifying information thereon may be placed into a bag through which the blister pack may remain readable. However, a blister package may not require an overpack when stored in an automated dispensing apparatus as the blister package may be sufficient for storage and handling by an end-of-arm-tool, as will be described further below.

Automated Dispensing System

Automated dispensing systems, as described herein, require an inventory of articles to be dispensed upon request. These dispensing systems must be periodically replenished in order to maintain the required inventory to fulfill orders as they are received. The inventory of articles stored at an automated dispensing apparatus may be stored in overpacks, such as those described above, or in the article's native packaging, such as a blister package for a unit dose of medication, an ampoule, a box, a bag, etc.

Figure 12:
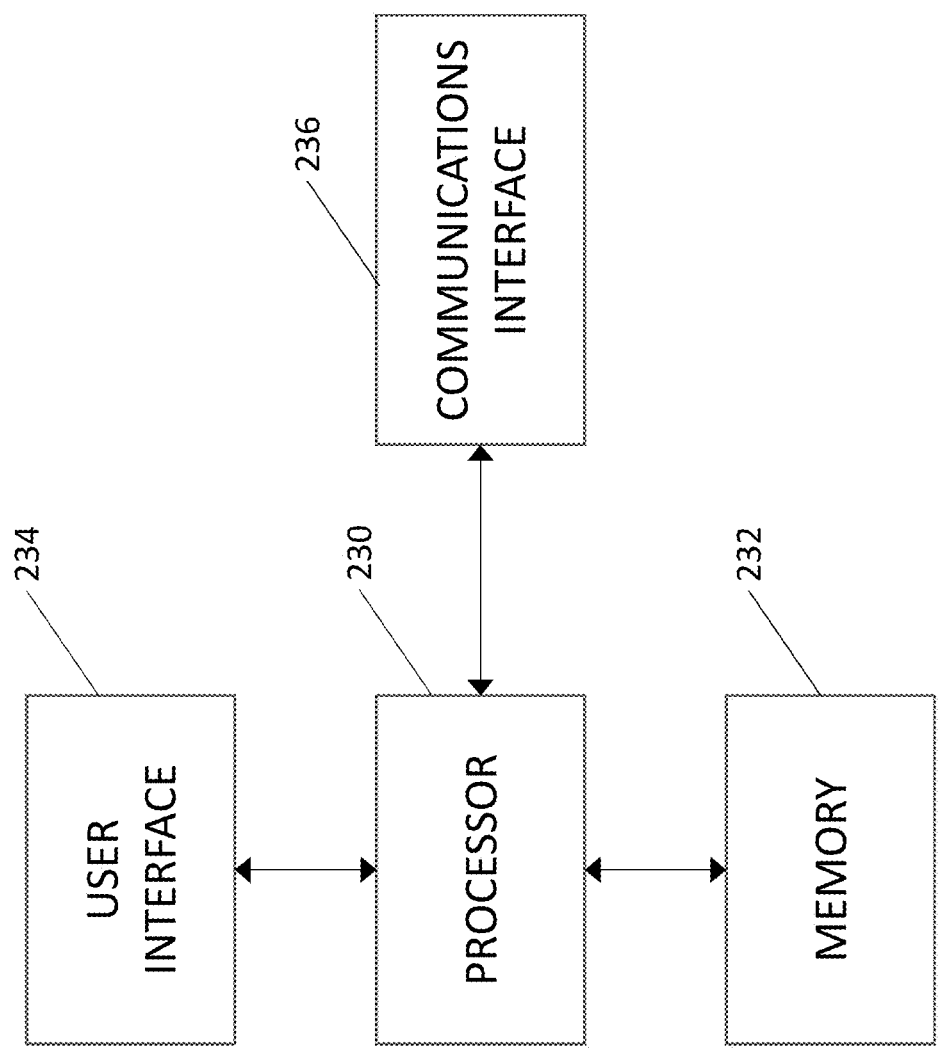
FIG. 12 is a block diagram of an example apparatus which may be implemented as a controller according to an example embodiment of the present invention.

An automated dispensing system may require a controller configured to control the functions of the automated dispensing. The controller may be configured in a variety of manners, an example of which is illustrated in FIG. 12. The controller of example embodiments may include processing circuitry. The processing circuitry may be configured to perform actions in accordance with one or more example embodiments disclosed herein. In this regard, the processing circuitry may be configured to perform and/or control performance of one or more functionalities of the handling, storing, or distributing of articles such as medications and/or supplies in accordance with various example embodiments. The processing circuitry may be configured to perform data processing, application execution, and/or other processing and management services according to one or more example embodiments. In some embodiments, computing device or a portion(s) or component(s) thereof, such as the processing circuitry, may be embodied as or comprise a circuit chip. The circuit chip may constitute means for performing one or more operations for providing the functionalities described herein.

A schematic illustration of an apparatus which may be implemented as a controller of an automated dispensing system is illustrated in FIG. 12. As shown, in some example embodiments, the processing circuitry may include a processor 230 and, in some embodiments, may further include memory 232. The processing circuitry may be in communication with, include or otherwise control a user interface 234 and/or a communication interface 236. As such, the processing circuitry may be embodied as a circuit chip (e.g., an integrated circuit chip) configured (e.g., with hardware, software, or a combination of hardware and software) to perform operations described herein.

The processor 230 may be embodied in a number of different ways. For example, the processor may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of a system for handling, storing, transporting, or distributing medication as described herein. The plurality of processors may be embodied on a single computing device or distributed across a plurality of computing devices. In some example embodiments, the processor may be configured to execute instructions stored in the memory or otherwise accessible to the processor. As such, whether configured by hardware or by a combination of hardware and software, the processor may represent an entity (e.g., physically embodied in circuitry—in the form of processing circuitry) capable of performing operations according to embodiments of the present invention while configured accordingly. Thus, for example, when the processor is embodied as an ASIC, FPGA, or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 232 may include one or more non-transitory memory devices such as, for example, volatile and/or non-volatile memory that may be either fixed or removable. In this regard, the memory 232 may comprise a non-transitory computer-readable storage medium. It will be appreciated that while the memory 232 is illustrated as a single memory, the memory may comprise a plurality of memories. The plurality of memories may be embodied on a single computing device or may be distributed across a plurality of computing. The memory may be configured to store information, data, applications, instructions and/or the like for enabling embodiments of the present invention to carry out various functions in accordance with one or more example embodiments. For example, the memory may be configured to buffer input data for processing by the processor. Additionally or alternatively, the memory may be configured to store instructions for execution by the processor. As yet another alternative, the memory may include one or more databases that may store a variety of files, contents, or data sets. Among the contents of the memory, applications may be stored for execution by the processor to carry out the functionality associated with each respective application.

A user interface 234 of example embodiments, such as the user interface of a user module of an automated dispensing system, may be in communication with the processing circuitry to receive an indication of a user input at the user interface and/or to provide an audible, visual, mechanical, or other output to the user. As such, the user interface may include, for example, a user input interface 234 such as a keyboard, a mouse, a joystick, a display, a touch screen display, a microphone, a speaker, and/or other input/output mechanisms. As such, the user interface may 234, in some example embodiments, provide means for user control of embodiments of the present invention. In some example embodiments in which the invention is embodied as a server, cloud computing system, or the like, aspects of user interface may be limited or the user interface may not be present. In some example embodiments, one or more aspects of the user interface may be implemented on a user terminal. Accordingly, regardless of implementation, the user interface may provide input and output means to facilitate handling, storing, transporting, or delivery of medication in accordance with one or more example embodiments.

The communication interface 236 may include one or more interface mechanisms for enabling communication with other devices and/or networks. In some cases, the communication interface may be any means such as a device or circuitry embodied in either hardware, or a combination of hardware and software that is configured to receive and/or transmit data from/to a network and/or any other device or module in communication with the processing circuitry. By way of example, the communication interface 236 may be configured to enable embodiments of the present invention to communicate with application server(s) and/or networks and/or information databases. Accordingly, the communication interface may, for example, include supporting hardware and/or software for enabling communications via cable, digital subscriber line (DSL), universal serial bus (USB), Ethernet, or other methods.

Figure 13:
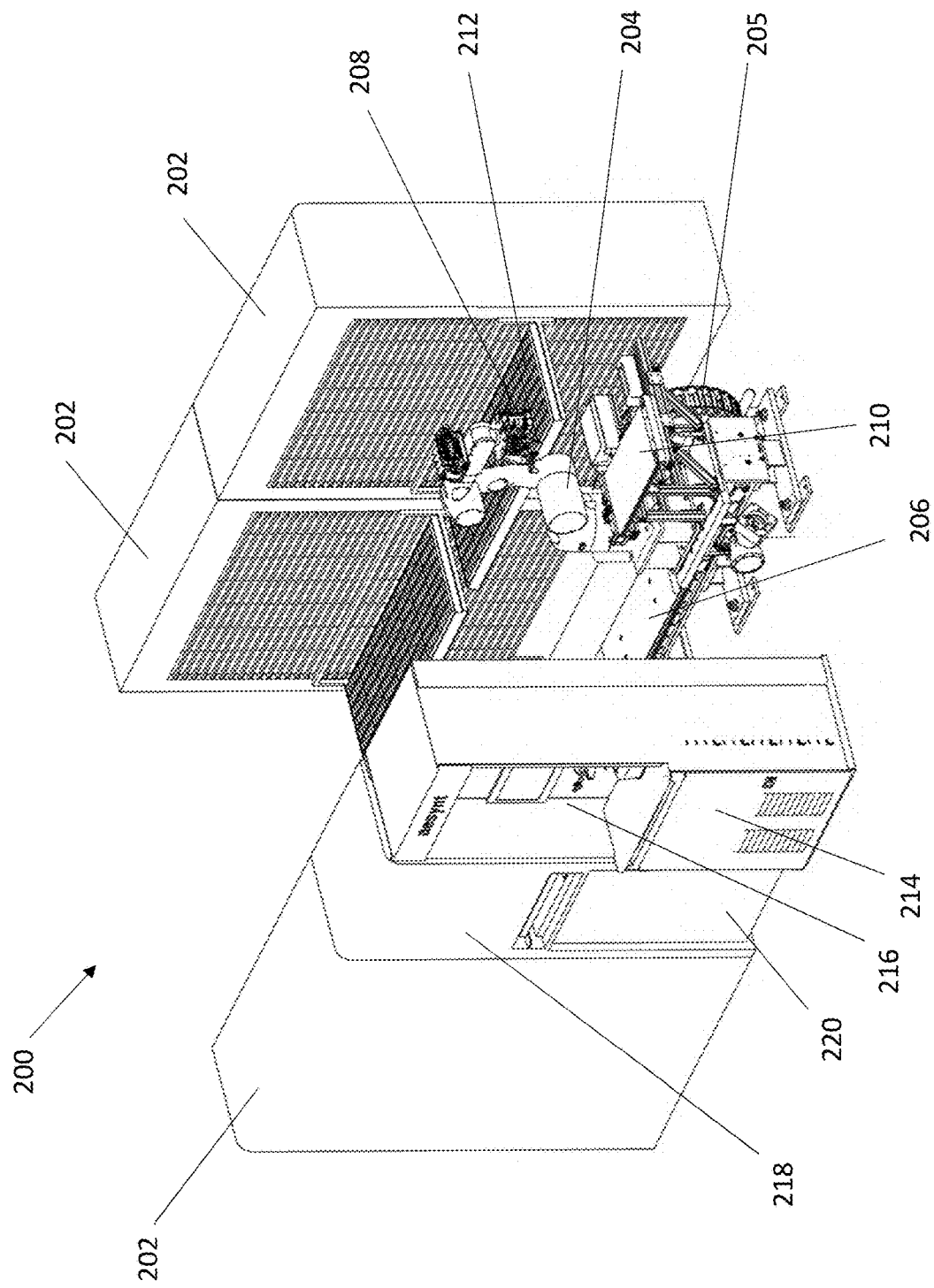
FIG. 13 is an example embodiment of an automated dispensing system according to an example embodiment of the present invention.

FIG. 13 illustrates an embodiment of an automated dispensing device system 200 according to an example embodiment of the present invention which may be controlled by a controller as described above with respect to FIG. 12. The illustrated embodiment includes a plurality of storage modules 202 arranged proximate a robot 204, which may be, for example, a six-axis robotic arm for retrieval and dispensing of articles as described further below. The robot 204 may be positioned on a track system 206 to allow the robot to move along the track providing greater access to the storage modules and allowing for expandability and modularity of the automated dispensing system. The robot 204 may include an end-of-arm tool 208 configured to attach to articles for retrieval, movement, and placement as necessary.

According to some embodiments, a work platform 210 may be provided to facilitate distribution of articles and the manipulation of articles as will be evident by the following disclosure. This work platform 210 may advantageously be coupled to the robot 204 and may traverse the track system 206 with the robot 204. The robot and work platform 210 may move along the track system in any conventional manner, such as with a pinion gear attached to the robot 204 base, with a rack gear extending along the track system. Optionally, the robot 204 may be belt-driven along the track system 206. Regardless of the motive mechanism of the robot along the track system, the position of the robot along the track system may be precisely monitored via embedded sensors or tags in the track system, displacement measurement of the robot 204, or any method of measuring a position along the track system accurately. The measurement of position along the track system 206 may facilitate accurate and repeatable movement of the robot 204 arm and positioning of the end-of-arm tool 208 to enhance accuracy of retrieval and movement of articles throughout the system 200. Electrical power, hydraulic power (if needed), pneumatic communication (e.g., vacuum or pressure), and hard-wired communications may be in communication with the robot 204 through an umbilical 205 which may bundle all necessary wiring, plumbing, etc. and may enable the robot 204 to traverse the track 206 while remaining in electrical and fluid communication with stationary equipment, such as a controller, hydraulic pump, pneumatic pump, and electrical power source, for example.

The storage modules 202 may be configured to store a plurality of articles, where each article is accessible to the end-of-arm tool 208 of the robot 204. While an arrangement of vertical shelves may be sufficient to store a plurality of articles, in order to increase the storage density, the available storage locations may extend horizontally to provide a substantial increase in storage capacity. To achieve this increased storage capacity, the storage modules may include a plurality of trays 212 which may be received within the storage modules 202 and may be configured to be moved between a storage position where the tray 202 is received within the storage module, and a retrieval position, in which the tray 212 is slid out from the storage module, accessible to the robot 204 and end-of-arm tool 208.

The automated dispensing device system 200 of example embodiments may further include a user module 214, which may be embodied by the controller of FIG. 12, or separate therefrom. While an automated dispensing device system 200 of example embodiments may be capable of being fully controlled through a remote interface or remote order request/fulfillment apparatus, such as a remote workstation, computer, controller, etc., the illustrated embodiment includes a user module 214 integrated with the automated dispensing device system. The user module 214 may include a user interface 216. The user interface 216 may include a means for providing information to a user, such as a display (e.g., light emitting diode (LED) display, organic LED display, liquid crystal display (LCD), plasma display, etc.), and a means for a user to enter information. The means for entering information may include a touch screen display, a keyboard, pointing device (e.g., mouse), a scanning device (e.g., barcode scanner or radio frequency identification (RFID) scanner, etc.), or the like. The user module 214 may be used to request the dispensing of articles, to review a queue of articles to be dispensed, to review errors or correct issues, etc.

The automated dispensing device system 200 of example embodiments may dispense articles in an automated manner, and may do so to a delivery device. For example, the automated dispensing device system 200 may dispense articles from the trays 212 to, for example, a bin. According to an example embodiment of an automated dispensing system of a healthcare facility, the system may receive a request to dispense one or more medications for a particular patient. In response, the robot 204 may advance along the track system 206 to a position for accessing a tray containing one or more of the requested medications. The tray 212 may be advanced to the retrieval position, either through a mechanism of the storage module 202, or using the robot 204 to move the tray to the retrieval position. Once the tray is in the retrieval position, the robot end-of-arm tool 208 may be moved by the robot 204 to a position above the location in the tray where one of the requested medications is stored. The end-of-arm tool 208 may retrieve the medication stored therein, and move the medication to a dispensing location. The dispensing location may be, for example, a patient-specific bin, which may be positioned on the work platform 210, or may be positioned at a dispensing area of a module of the system 200. Once the requested medications for the patient have each been retrieved and dispensed to the patient-specific bin, the bin may be moved to a location for transport to the patient. One such example of a transport device is a cart, such as a nurse cart.

The illustrated embodiment of FIG. 13 includes a cart module 218 and a cart 220. The cart 220 may be received within the cart module 218 from a position outside of the automated dispensing system 200, such that movement of the cart into and out of the cart module may not disrupt the operation of the robot 204 within the system. The cart may be accessible within the cart module 218 to the robot 204. The robot may move the patient-specific bin containing the requested medications to the cart 220 of the cart module 218 such that the patient specific bin is ready for transport to the patient with the cart 220. Optionally, the cart may include a plurality of storage locations therein and the robot 204 may dispense the medications requested for a patient to a storage location of the cart without requiring a separate patient-specific bin.

According to example embodiments described herein, the automated dispensing system 200 may dispense a plurality of articles, such as medications, to a transport device, such as a cart 220, without requiring manual intervention. This automated dispensing may be achieved through proper identification of articles as they are received in the automated dispensing system 200 and as they are retrieved within the system for dispensing.

Figure 14:
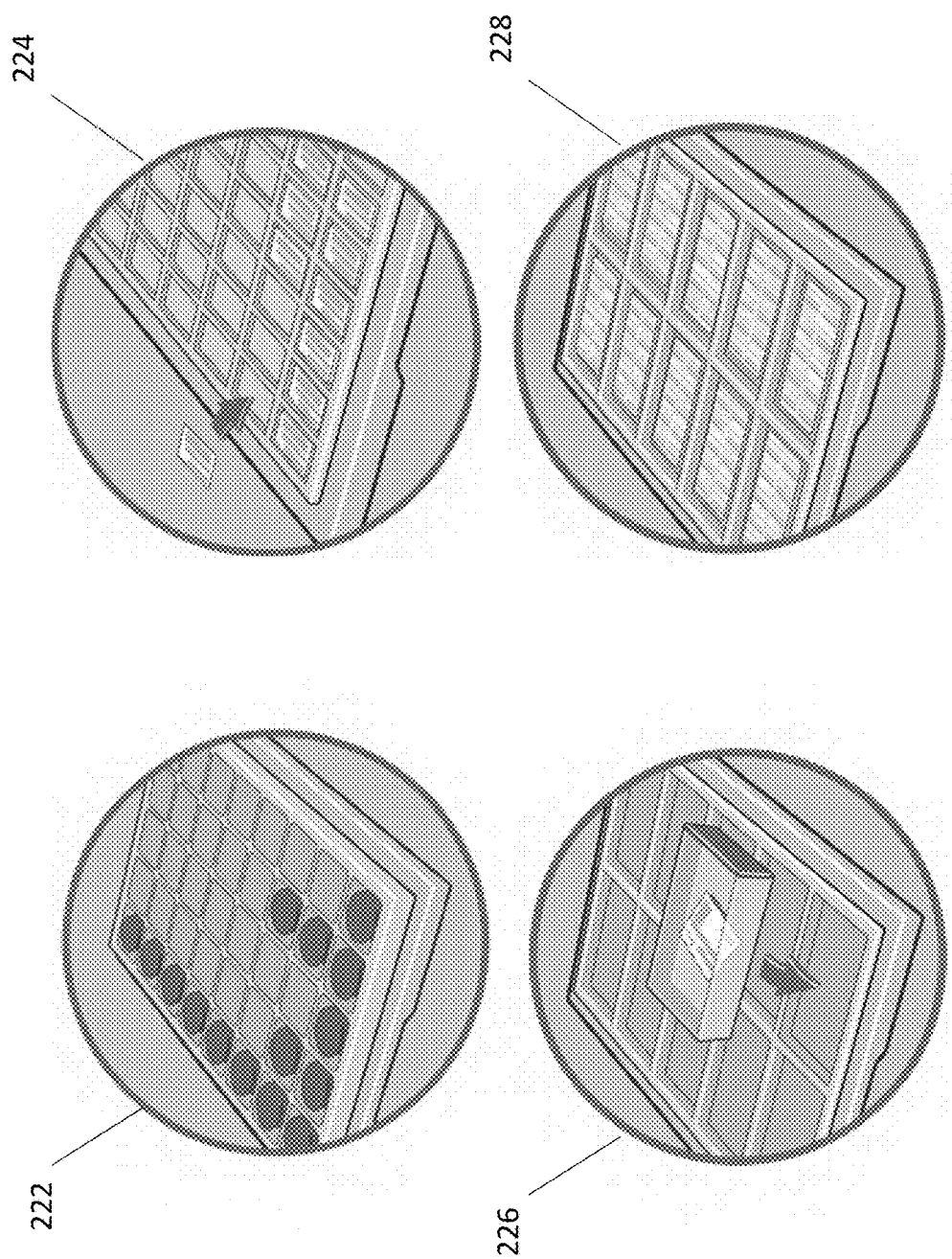
FIG. 14 illustrates several example embodiments of tray configurations according to the present invention.

Each tray 212 within each storage module 202 may include a plurality of locations, where each location has a unique identification. The locations may be uniquely identified based on an identifier, such as a barcode or RFID tag at the location, or uniquely identified by coordinates (e.g., Cartesian coordinates) within the tray, for example. The trays may have various different configurations in order to accommodate different types of articles stored therein. FIG. 14 illustrates several potential configurations of trays according to example embodiments described herein. A tray may be configured to hold a plurality of cups, such as medication cups as shown at 222. A tray may be configured to hold a plurality of blisters, such as medication unit dose blister packages as shown at 224. A tray may be configured to hold a plurality of bins which may be of uniform or different sizes as shown at 226. These bins may be clear to facilitate identification of the articles contained therein as described further below. And trays may be configured to hold a plurality of cards, such as a card containing a plurality of individual unit dose blister packages as shown at 228. Trays may be configured in a variety of manners to hold any type of article requiring automated dispensing. Further, trays may be configured to hold various different form factors, including a combination of any of the tray configurations of FIG. 14 implemented in a single tray. The pockets of a tray may optionally be lined with a relatively higher friction material, particularly over smooth plastic tray pockets. This may enable example embodiments to maintain the position of an article loaded into a pocket, such as a medicine vial in a label-up position, and mitigate the effects of vibration and movement of the articles within the pocket to enable easier identification of the article in the pocket.

According to an example embodiment, each location of a tray may be uniquely identified such that a position of the location within the tray is known. The geometry of a tray and the locations therein may be stored within a memory, such as memory 232 of the controller illustrated in FIG. 12. Each tray may be unique such that the memory 232 includes a unique layout and geometry together with location identifiers for each tray. In such an embodiment, each tray may include a unique identifier, such as a barcode, 2-dimensional barcode, an RFID tag, etc. Optionally, there may be a specific number of configurations of trays, and each configuration may have a unique identification. In such an embodiment, the identification of a tray may only provide the configuration information, while the location of the tray within the storage module may be stored within the memory of the controller 232 to facilitate retrieval of articles from the tray.

The trays 212 of example embodiments may be maintained within or associated with a particular storage module, such that the trays are replenished for dispensing of articles therefrom. However, according to some embodiments, the trays may be removable from the storage modules and replenishment may occur through replacement of trays within a storage module. In such a case where trays are removable from a storage module, an identification of a tray 212 may be read by a device, such as a scanning device, upon receipt into a storage module such that the controller can associate a specific tray with a specific location within the automated storage device.

As articles are dispensed from automated dispensing systems as described herein, replenishment of articles is required to maintain an inventory of articles for dispensing. The replenishment is an operation that may occur in down-time between dispensing operations, which may occur overnight in a healthcare facility where fewer medications are being dispensed, for example. Various methods for replenishment may be used to replenish the automated dispensing systems described herein, and replenishment in a fast and efficient manner may be important in implementations in which there is little downtime over which replenishment may occur.

The automated dispensing system 200 of example embodiments may also provide automated replenishment using the robot 204 and end-of-arm tool 208 as described herein. Replenishment may occur through replacement of entire trays 212, or portions thereof. For example, a replenishment cart may be received within cart module 218, where the replenishment cart includes a plurality of trays stored therein. These trays may include a plurality of storage locations as described above with respect to FIG. 14. The trays may be removable from the cart, such that a tray may be retrieved by the robot 204. The trays of the replenishment cart may be of the same size as the trays 212 of the storage module 202, and may be interchangeable with the trays of the storage module. In such an embodiment, replenishment may occur through the swapping of trays within the storage module with a replacement tray from the replenishment cart. However, according to some embodiments, the replenishment cart may not be of sufficient size to hold trays of the same size as those in the storage modules.

The trays of the storage modules may be relatively large, such that replenishment may occur on only a portion of the trays of the storage modules. In such an embodiment, the trays 212 of the storage modules 202 may include inserts, wherein the inserts include a plurality of locations, and each tray may include several inserts. In such an embodiment, inserts of the trays may be swapped during replenishment. For example, a tray 212 of the storage module may be configured to hold three inserts. An insert that is scheduled for replenishment (because the insert is empty, mostly empty, or contains articles that are now or will soon expire, etc.) may be removed from a tray 212 of the storage module 202 by the robot 204 using the end-of-arm tool 208. The replenishment cart received at the cart module 218 may include an insert to replace the removed insert. The robot 204 may retrieve the replenishing insert and place the replenishing insert into the tray 212. In such an embodiment, each insert may be individually identified, with locations of the inserts known and the contents thereof stored in a database, such as in memory 232 of the controller. Such inserts may promote the bulk replenishment of articles.

According to some embodiments, replenishment of articles may occur on a unit-by-unit basis. A replenishment cart may be received at the cart module 218, and may include a tray of articles for replenishment of the system 200. The tray may be removed from the replenishment cart, and placed into a location within the automated dispensing system 200 for access by the robot 204 and the end-of-arm tool 208, such as on work platform 210. The robot 204, using the end-of-arm tool 208 and advancing along the track system 206, may retrieve articles from the replenishment tray and place them into locations of the trays 212 of the storage unit. As this is done, a location and identification of the article may be stored by the controller, such as in memory 232.

According to some embodiments, the robot 204 may also be configured to, at the instruction of the controller, to move articles between different storage locations within one or more trays 212 of the storage modules 202. This may be performed to consolidate articles, or to place articles into strategic positions based on other articles that are likely to be retrieved with those articles. For example, if a first medication often causes a side effect that is treated with a second medication, the first and second medications may be placed proximate one another within a tray 212 of a storage module 202 as it is likely that both medications will require retrieval at the same time. Automated storage systems of example embodiments may also have trays or zones for which retrieval of articles is more efficient. For example, a tray that is at a height similar to that as the middle of the robot 204 height may be more efficiently accessed than a tray that is at the top or bottom of the robot's travel. High-volume articles, or articles that are frequently used, may be positioned in these more efficiently accessed areas to promote faster throughput of the automated dispensing system. The high volume articles may change seasonally (e.g. allergy medications) such that repositioning of medications may be performed by the robot 204 by instruction from the controller to optimize the organization of articles in the storage modules. Periodically, the robot 204, at the instruction of the controller, may de-fragment or defrag the stored articles by consolidating articles into a more condensed area of storage. Sparsely distributed articles may be brought together to promote efficient retrieval and dispensing of articles.

The robot 204 may include a scanner, such as a barcode scanner, RFID tag scanner/reader, etc., to read the identification of articles as they are retrieved and/or placed into storage locations. Further, this scanner may read the identification of trays 212, tray inserts, and/or locations within the trays or inserts. The scanner may be used to identify articles that are being dispensed or replenished in order to ensure accuracy and that the article that is stored in a particular location of the storage module is consistent with the article that is anticipated.

According to some embodiments, the scanner may be an image capture device, to capture images of a barcode or identifier and use the image, through barcode analysis or optical character recognition, to deduce the identity of the scanned image. In such an embodiment, the robot 204 may use the image capture device as a vision guidance system to facilitate learning locations within trays for articles. The image capture device may enable the robot to determine a centroid of an article in order to best grip the article to retrieve it. Further, the image capture device may enable the robot 204, through use of the controller, to determine an orientation of an article within a tray such that the end-of-arm tool can be properly positioned to retrieve the article based on the determined orientation.

While the scanner or image capture device of example embodiments may be used to determine the identification of an article, some articles may not have identifying indicia that is easily read, particularly those in which orientation of an article may obscure the identifying indicia. One such example embodiment may include a medication vial, where a barcode is disposed on one side of a substantially cylindrically shaped vial. If the barcode is not positioned in a manner in which the barcode can be read while the vial is in a tray 212 of the storage module, 202, alternative methods of identification may be required.

Figure 15:
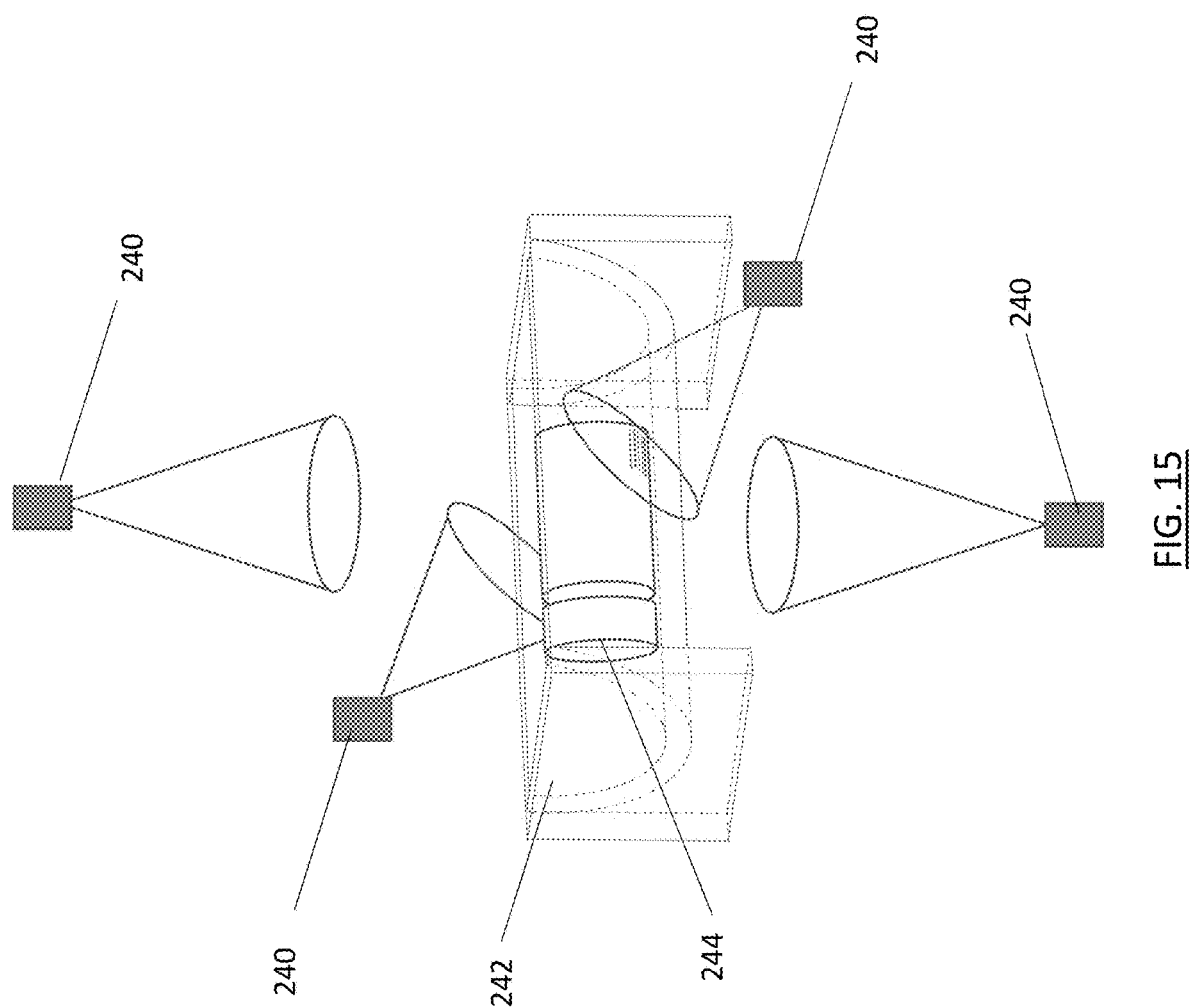
FIG. 15 is an example representation of a scanning station for the identification of articles according to an example embodiment of the present invention.

Some embodiments described herein may include bins configured to facilitate the identification of articles that may be unidentifiable based on their orientation. Trays 212 may contain a plurality of bins, such as the bins of the tray illustrated in 226 of FIG. 14. The bins may be transparent and removable from the tray such that a retrieved bin may be provided to an identification station for determination of an identification. FIG. 15 illustrates an example embodiment of a bin 242 as removed from a tray 212. The bin may be moved to a station within the automated dispensing system 200 by the robot 204 where several scanning devices 240 are positioned. The scanning devices may be barcode readers or image capture devices, for example. In response to the robot 204 inserting the bin 240 into the identification station, the scanning devices 240 may scan the bin for the contents, through the transparent material of the bin. A barcode or other indicia disposed on the vial 244 may be scanned by at least one of the scanning devices 240 and the information provided to the controller for identification. The bin 242 of the illustrated embodiment includes a curved profile along its length lacking corners of a conventional rectangular bin. The curved, transparent profile may promote easier scanning of the indicia on the vial 244 by providing a substantially undistorted view of the indicia about the vial, as would be present if scanning indicia through the corner of a rectangular bin.

Figure 16:
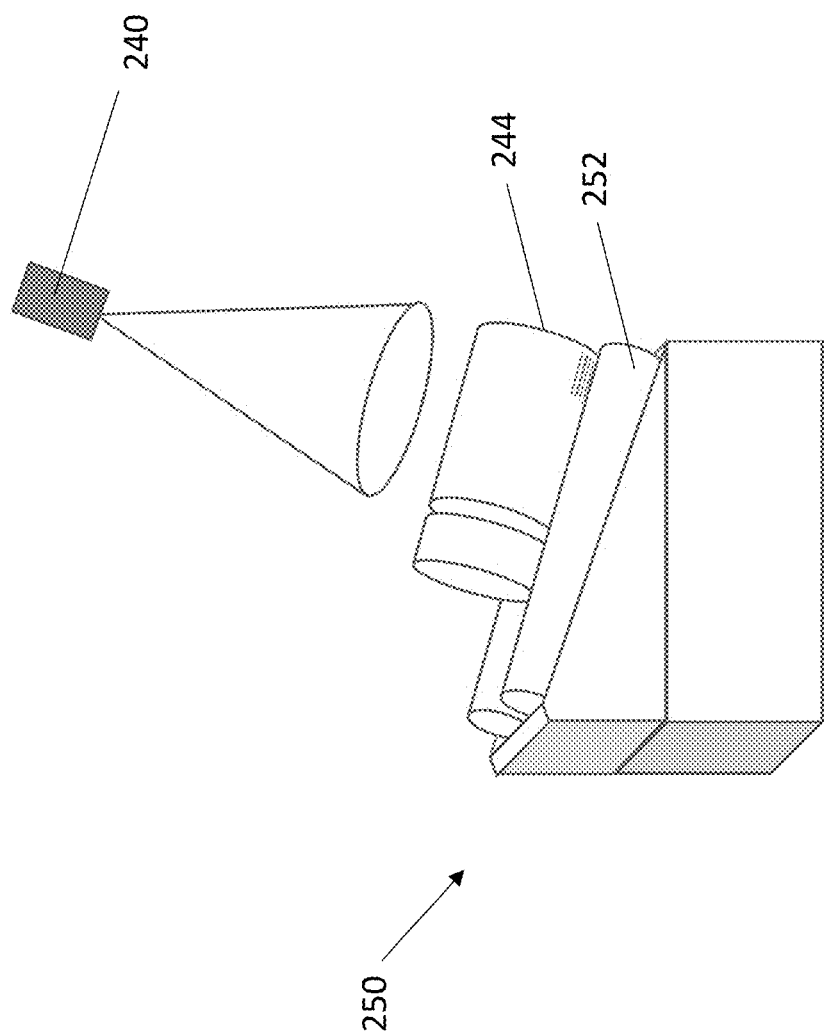
FIG. 16 is a vial roller according to an example embodiment of the present invention.

According to example embodiments of automated dispensing systems that commonly dispense articles of a cylindrical or substantially cylindrical shape, where the identifying indicia may not be visible to a scanner of the end-of-arm tool while the article is resting in a location within a tray, a rolling mechanism may be employed to rotate the cylindrical article 244 while a scanning device 240 scans the article as depicted in FIG. 16. The article roller 250 of FIG. 16 includes a pair of rollers 252 configured to rotate the article 244 about its major axis in order for the scanning device 240 to view the entire major surface of the article. This may enable the scanning device to read the identifying indicia from the article. As different sizes of cylindrical articles may be dispensed from automated dispensing systems, multiple article rollers 250 may be used, with varying size rollers or gaps between the rollers 252 in order to securely rotate articles of other sizes. Optionally, the article roller 250 may include rollers that have a variable width, such that the distance between the rollers can be adjusted by the controller to accommodate a retrieved article. The article roller may be positioned conveniently to the robot 204 and the end-of-arm tool 208, such as on work platform 210.

While an article roller 250 may be used to virtually unroll a label as the cylindrical article is rotated on the rollers 252, example embodiments may optionally capture images from three different positions around a retrieved article in order to read any indicia from the article. A first image capture device or camera may be captured from the end-of-arm-tool as it is positioned to retrieve an article. This image may be an image of a top side of an article. The robot 204 may retrieve the article from a pocket, such as a pocket of a tray, and advance the article to a position in which two additional image capture devices may capture images from two positions below the article. The image capture devices may be positioned in such a way as to capture 360 degrees around the article to ensure any indicia on the label may be captured. This may involve three or more image capture devices, where the image capture devices capture up to 120 degrees of a surface of an article. The images of the underside of the article may be captured at a specific point during the retrieval as the article passes through an image capture area, or optionally the robot may advance the end-of-arm-tool holding the article to a station to specifically capture the images that may be used to identify the article in a manner similar to that described with respect to FIG. 15.

Scalable Modular Architecture

Figure 17:
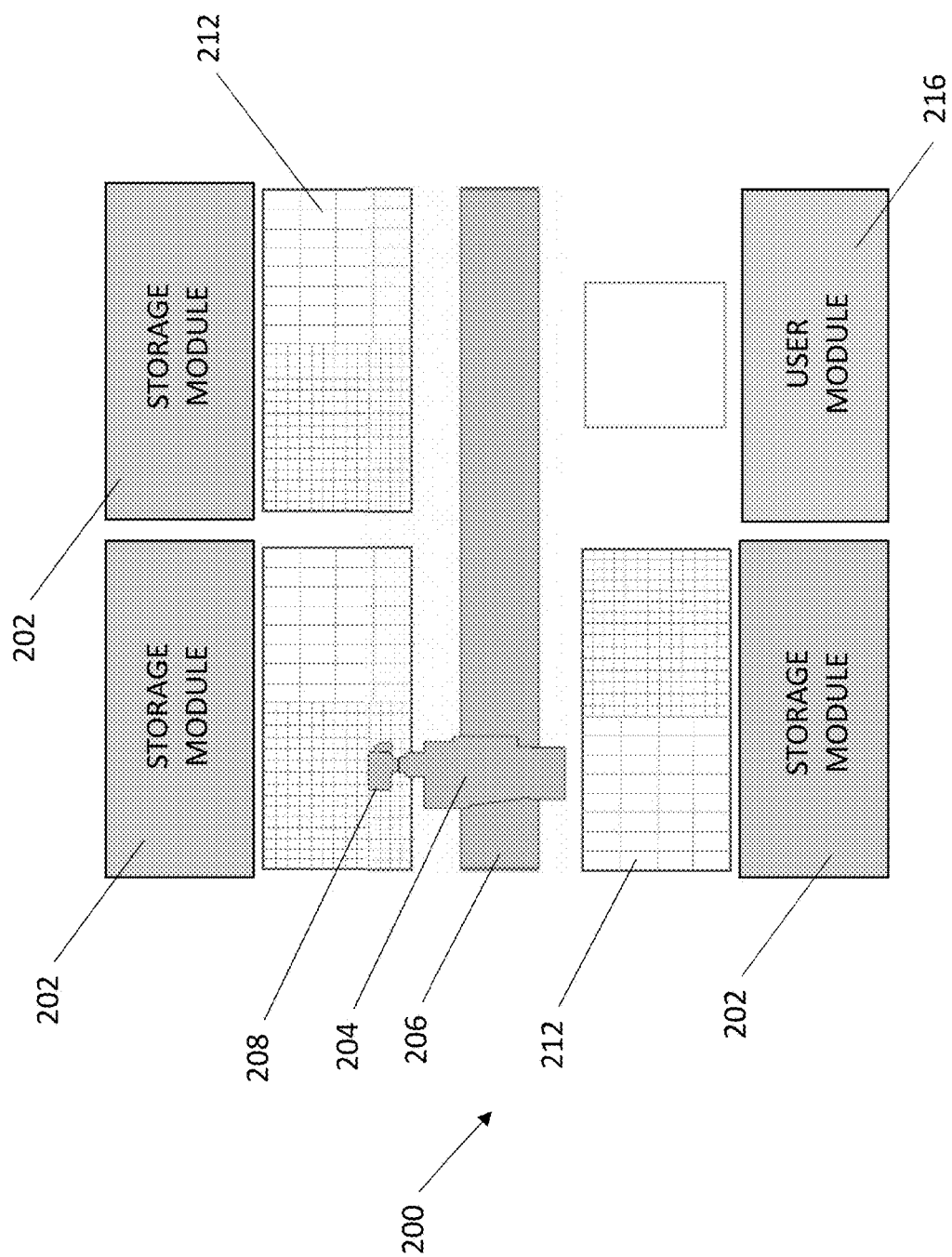
FIG. 17 is a plan view of a modular automated dispensing system according to an example embodiment of the present invention.

The illustrated embodiment of FIG. 13 depicts three storage modules 202, a cart module 218, and a user module 214. The cart module may be incorporated with the user module according to some embodiments described herein. FIG. 17 illustrates a plan view of the configuration depicted in FIG. 13 of the automated storage system 200. The illustrated system of FIG. 17 includes the three medication storage modules 202, the user module 216 (including cart module 218), the track system 206, the robot 204, and the end-of-arm tool 208. FIG. 4 illustrates the storage modules 202 with a drawer from each module extended in the retrieval position to illustrate the spatial relationship between the modules, the track system 206, and the robot 204. As shown, the robot 204 and the end-of-arm tool 208 can access each storage compartment within each tray 212.

Figure 18:
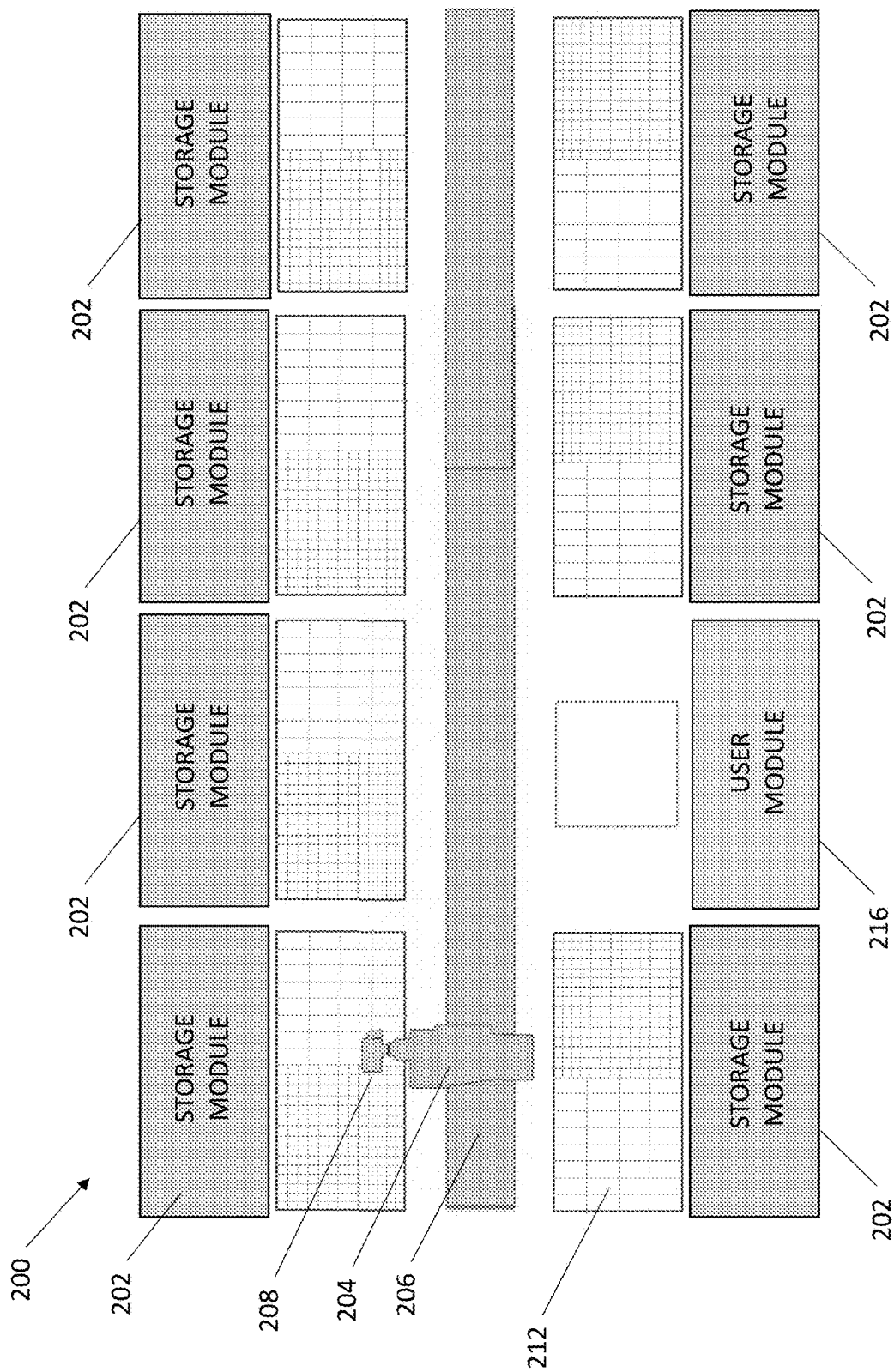
FIG. 18 is another plan view of a modular automated dispensing system according to an example embodiment of the present invention.

While the illustrated embodiment may provide a high-density solution for an automated dispensing system, where many articles can be stored for dispensing in a relatively small area, some implementations may require additional capacity. As such, embodiments described herein may be modular in nature and may be scalable to accommodate implementations in a wide variety of environments. FIG. 18 illustrates another example implementation of embodiments of the present invention. As shown, four additional storage modules are included in the embodiment of FIG. 18, with an extended track system 206 such that the robot 204 can access the additional storage modules. This implementation provides more than double the storage capacity of the embodiment of FIG. 17 while only doubling the size of the overall system. Further, embodiments described herein have a high storage density compared to other storage and automated dispensing options, such that the products stored for dispensing in the embodiments described herein represent a more efficient use of space, which can be limited in many healthcare environments.

Figure 19:
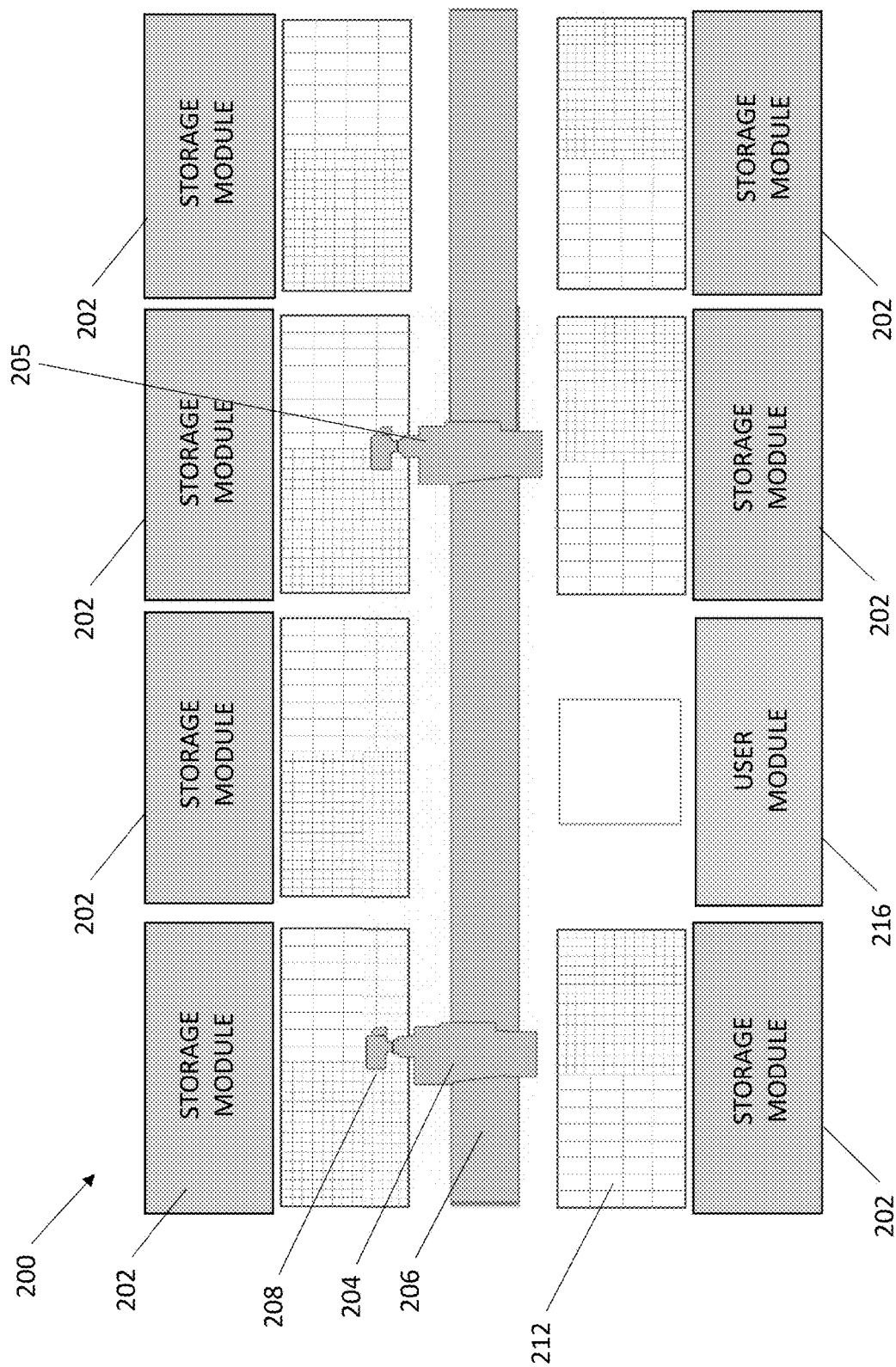
FIG. 19 is a plan view of a modular automated dispensing system having two robots according to an example embodiment of the present invention.

FIG. 19 illustrates another embodiment of the present invention featuring the automated dispensing system illustrated in FIG. 18; however, a second robot 205 has been added. The second robot 205 can be added to the same track system 206 on which the first robot 204 is operating, and the second robot can provide an increase in throughput by doubling the rate at which articles can be retrieved. The two robots can both be controlled by the same controller or separate controllers that are in communication with one another. The robots can communicate position along the track system 206 and be instructed to retrieve articles in such a way as to maximize the duty cycle of both of the robots, thereby maximizing the utilization of the available resources and increasing throughput.

As will be appreciated, the modular nature of example embodiments allows for the expansion and scalability of automated dispensing systems in a limitless fashion. Further, additional cart modules may be implemented to increase the amount of options for dispensing and/or restocking. For example, one robot can be restocking trays from a first cart module while another robot is dispensing articles to a second cart module.

Figure 20:
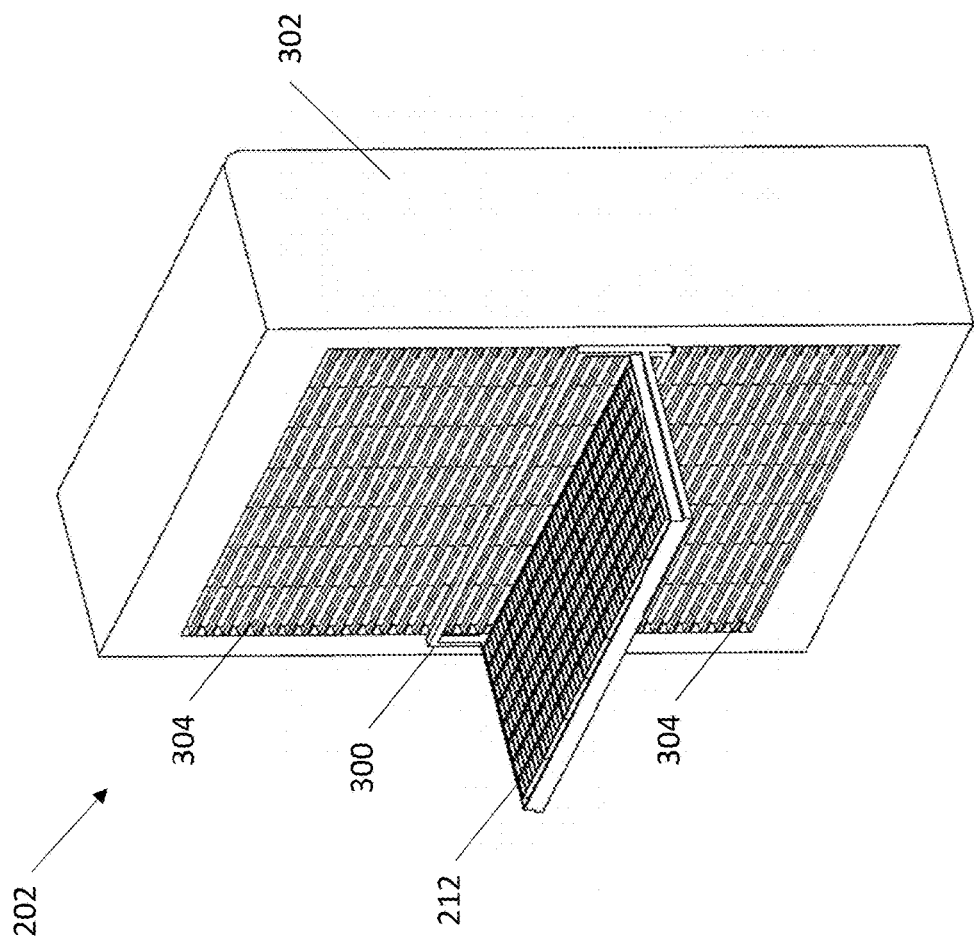
FIG. 20 is a storage module according to an example embodiment of the present invention.

FIG. 20 illustrates an example storage module according to an example embodiment provided herein. The example storage module may include a cabinet 302 from which the trays 212 extend when moved to the retrieval position illustrated. The cabinet may hold a large number of trays, and the spacing between trays may be determined based on the types of articles to be held in the trays. For example, if a tray is to hold only unit does of medications in blister packs, the tray may require only a relatively small vertical height for clearance within the cabinet 302. However, if a tray is to hold 1,000 mL bags of intravenous solutions, the vertical clearance required between adjacent trays may be substantially greater. While moving the trays 212 from a storage position (shown as trays 304) to a retrieval position (shown as tray 212) may enable a robot 204 to access the storage locations within the tray 212, greater storage capacity may be achieved if the trays are moved to a position that is more easily and efficiently accessible to a robot 204 and end-of-arm tool 208. For example, a tray elevator 300 may be employed to move trays in a vertical direction along the face of the cabinet 302 in response to the tray being moved to the retrieval position of tray 212. In this manner, the tray elevator 300 may move a tray from the top or bottom-most location to an access location which is a location that is more easily and more quickly reached by the robot 204.

Such tray elevators 300 as described herein may further enable cabinets 302 to be constructed to virtually any height, while being able to move the trays to a position on the storage module that is accessible to the robot 204. These tray elevators may move along tracks on or within the face of the cabinet 302 and may be driven, for example, by cables or gears to precisely move the tray to and from the position in which the tray is stored in the cabinet 302.

Figure 21:
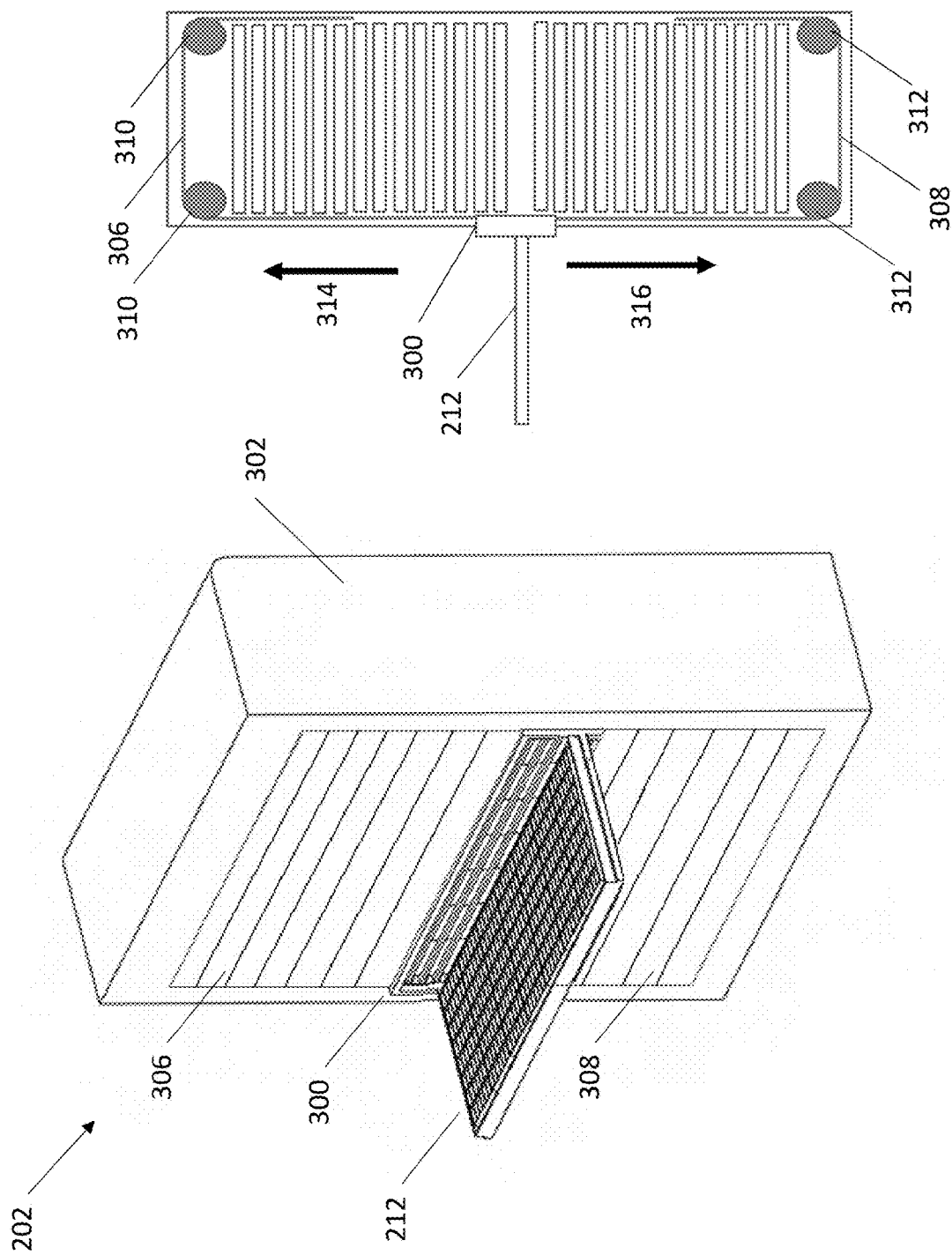
FIG. 21 is an illustration of a storage module having movable closures according to an example embodiment of the present invention.

Storage modules of example embodiments may require secure closures over the trays in order to keep temperature or humidity levels within required levels for the articles stored therein, or security of the stored articles may be a concern, such as in the case with narcotic medications. Embodiments described herein may include doors that cover trays that are in a stored position, such as trays 304 of FIG. 20. FIG. 21 illustrates a pair of door closures 306 and 308 that enclose trays that are not currently accessed by the tray elevator 300. The door closures may be similar to closures found on a roll-top desk, where the door is flexible along one axis, and "rolls" back into the cabinet as it is raised or lowered. FIG. 21 illustrates a section view of the storage module illustrating the upper door closure 306 that is received by the cabinet 302 over upper rollers 310, while lower door closure 308 is received by the cabinet 302 over lower rollers 312. As the tray elevator 300 moves up along the direction of arrow 314, more of upper closure 306 rolls back into the cabinet 302 over rollers 310, while more of lower closure 308 is moved from within the cabinet and presented in the front of the cabinet, below the tray elevator 300. Similarly, when the tray elevator moves down along arrow 316, lower closure 308 rolls back into the cabinet 302 over rollers 312, while upper closure 306 rolls out from within the cabinet and is presented at the front of the cabinet above the tray elevator 300. These upper and lower closures preclude trays that are not presently being accessed by the tray elevator 300 from being accessed manually or otherwise.

Storage modules of example embodiments may be provided with access outside of the area in which the robot 204 or robots are moving. During operation of the robots, the area between the storage modules where the robot operates may be closed to operators to prevent an operator from being injured by the robot or tray elevators. However, it may be desirable to enable access to a tray while the automated dispensing system is actively dispensing articles. As such, access to trays from outside the automated dispensing system may be provided. The trays may be available to slide out the opposite side from that shown in FIGS. 20 and 21. This may enable an operator to manually check or verify articles, or to manually replenish any articles urgently needed. Storage modules may include a tray elevator on the back of a storage module to more conveniently present a tray to a user outside of the automated dispensing system. Further, the closures illustrated in FIG. 21 and described above may be implemented on the back of a cabinet for security and/or safety. Should closures be used on both the front and rear of a cabinet, rather an implementation may use a closure similar to a roll-up door, where the upper closure 306 of FIG. 21 would be received around a single roller 310 as it the closure is retracted.

Access to the contents of the dispensing system may be desirable when the system is down for service or if technical issues arise. In such an instance, the module of the system that is accessible from outside of the system may contain a typical supply of medications that may be needed for a period of time, such as 24 hours. This may enable a facility to remain fully operational when the dispensing system is not functioning. Further, the system may configure itself for such scenarios. If a patient in the facility has been prescribed a medication that is not commonly use, the dispensing system may move a supply of that medication type to the unit that is accessible from outside of the dispensing system to prepare for potential unexpected down time.

Storage Module Types

Figure 22:
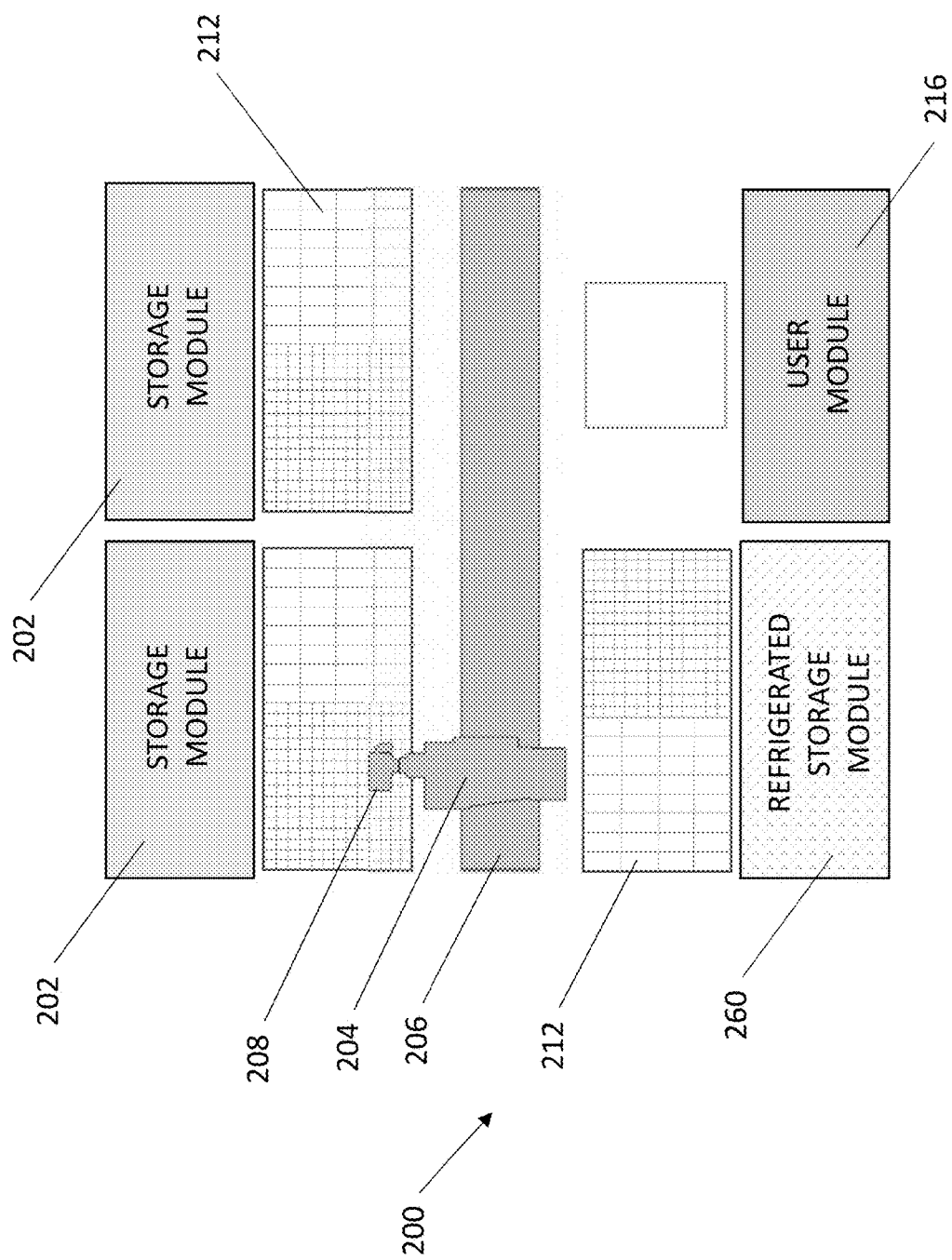
FIG. 22 illustrates a plan view of a modular automated dispensing system having a refrigerated storage module according to an example embodiment of the present invention.

Example embodiments of storage modules described above may be specifically configured for storage of a specific category of articles. For example, some medications in a healthcare environment are required to be kept below room temperature such that refrigerated storage may be required. The modularity of the automated dispensing system may be configured to receive a refrigerated storage module 260, as depicted in FIG. 22. While an entire module is depicted in FIG. 22 as refrigerated, a storage module may be partially refrigerated in dependence upon the required refrigerated storage capacity. The refrigerated storage module may function in substantially the same manner as the storage modules 202. However, the refrigerated storage module may benefit from the implementation of the upper closure 306 and lower closure 308 described above with respect to FIG. 21, even if the remaining storage modules do not use such closures. The upper closure 306 and lower closure 308 of a refrigerated storage module 260 may be insulated or provide insulating properties to the contents of the refrigerated storage module. In this manner, the contents of a refrigerated storage module may be maintained at an appropriate temperature more efficiently and more consistently, thereby prolonging the life of the articles stored therein.

Figure 23:
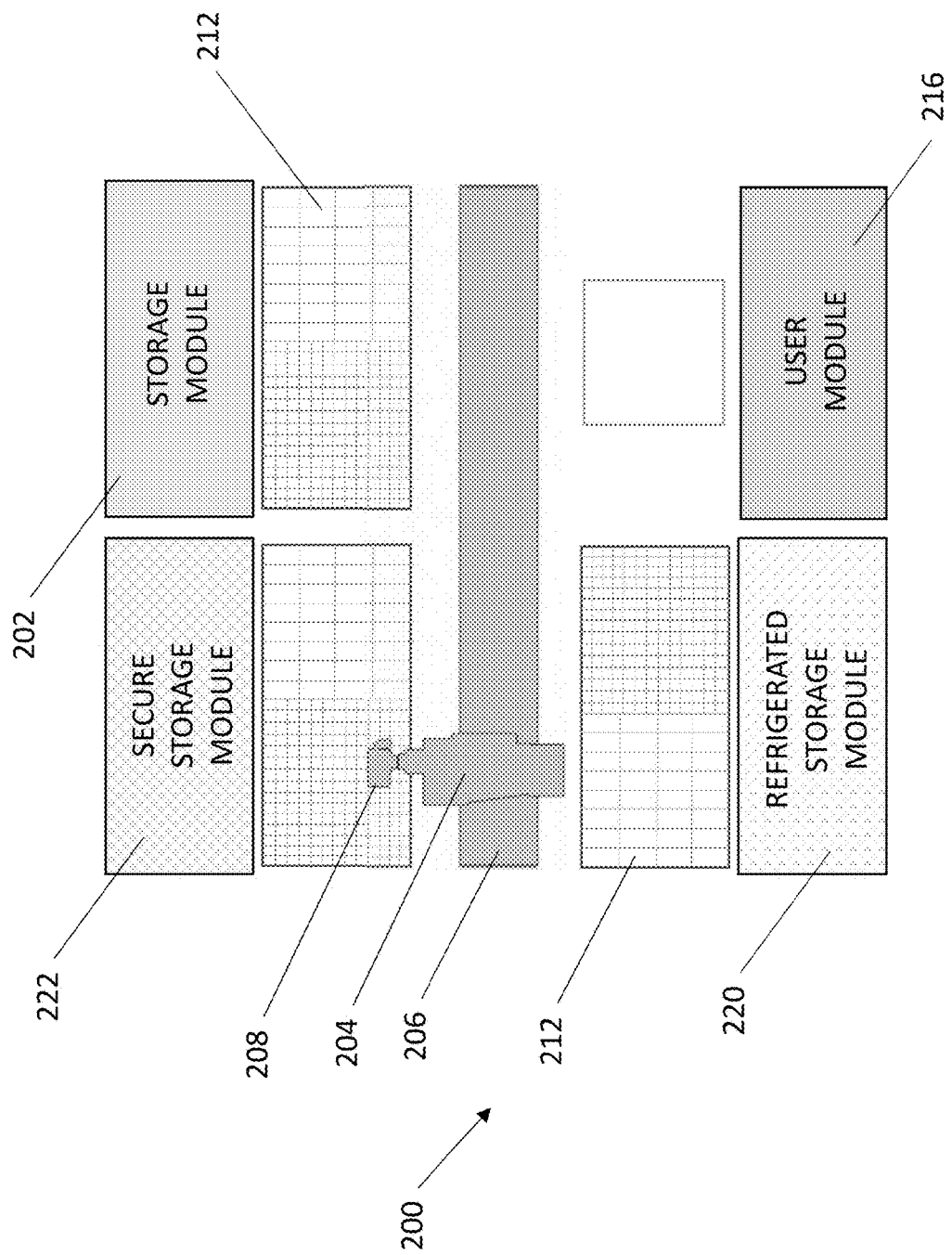
FIG. 23 illustrates a plan view of a modular automated dispensing system having a secure storage module according to an example embodiment of the present invention.

Other article types may also require specific storage needs. For example, articles that are subject to inventory regulations, such as narcotics, may require security protocols that are not otherwise required for non-narcotic medications. FIG. 23 illustrates an example embodiment of an automated dispensing system that includes both a refrigerated storage module 260 and a secure storage module 262. The secure storage module may include an upper closure 306 and a lower closure 308, as illustrated in FIG. 21, in order to preclude access to trays that are behind the closures. Optionally, each tray may be equipped with a locking mechanism to preclude removal of the tray from the secure storage module 262 without proper authorization. Manual entry to the secure storage module may thus be precluded when a technician or other personnel are within the automated dispensing system (e.g., during system downtime) and authorization is not granted. This secure storage mechanism may be adapted to conform to local, regional, or national regulations relating to the types of articles stored therein. Access may be granted to the secure storage module 262 via user module 216 or during routine article dispensing using the robot 204.

Figure 24:
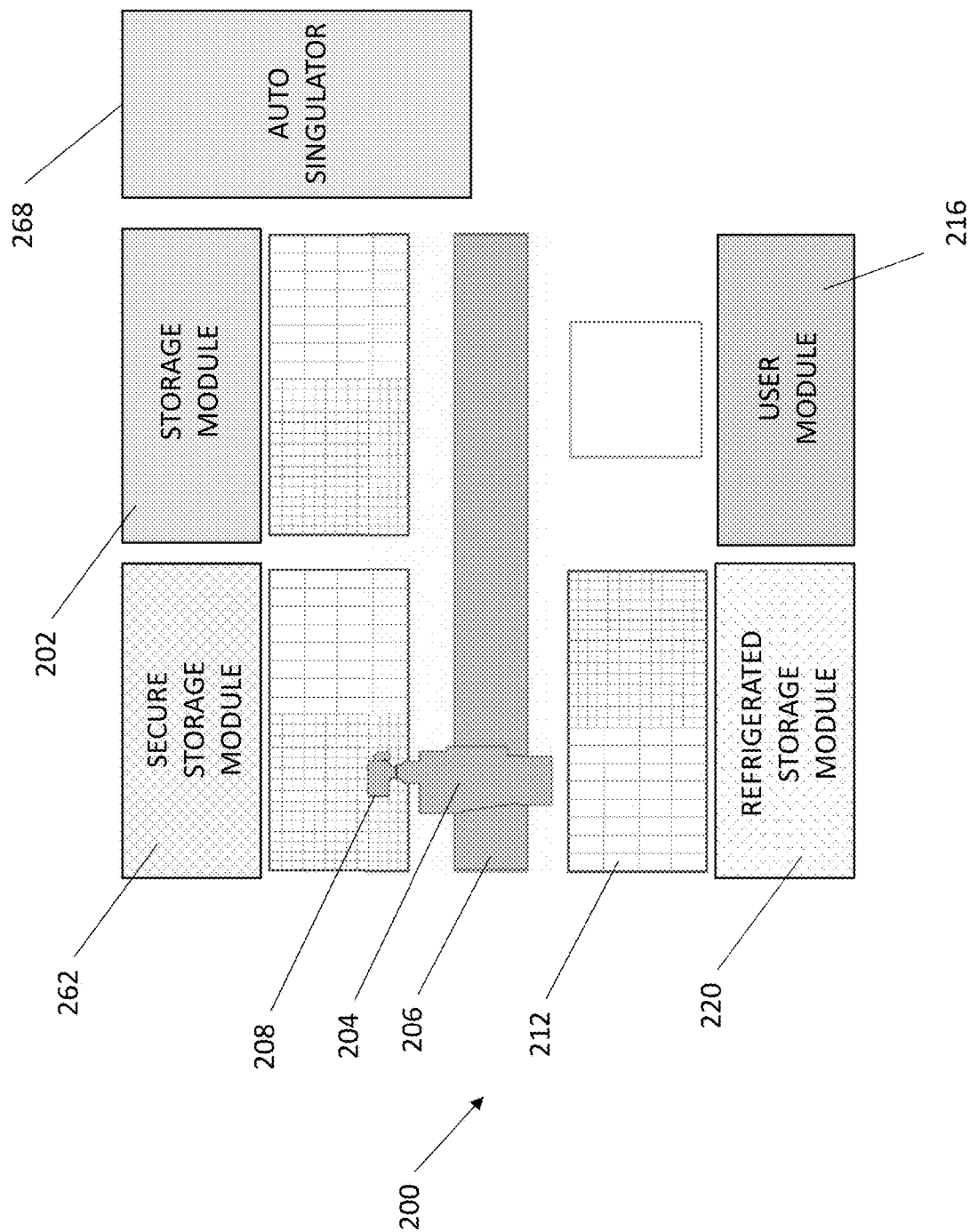
FIG. 24 illustrates a plan view of a modular automated dispensing system having an automated singulator module according to an example embodiment of the present invention.
Figure 25:
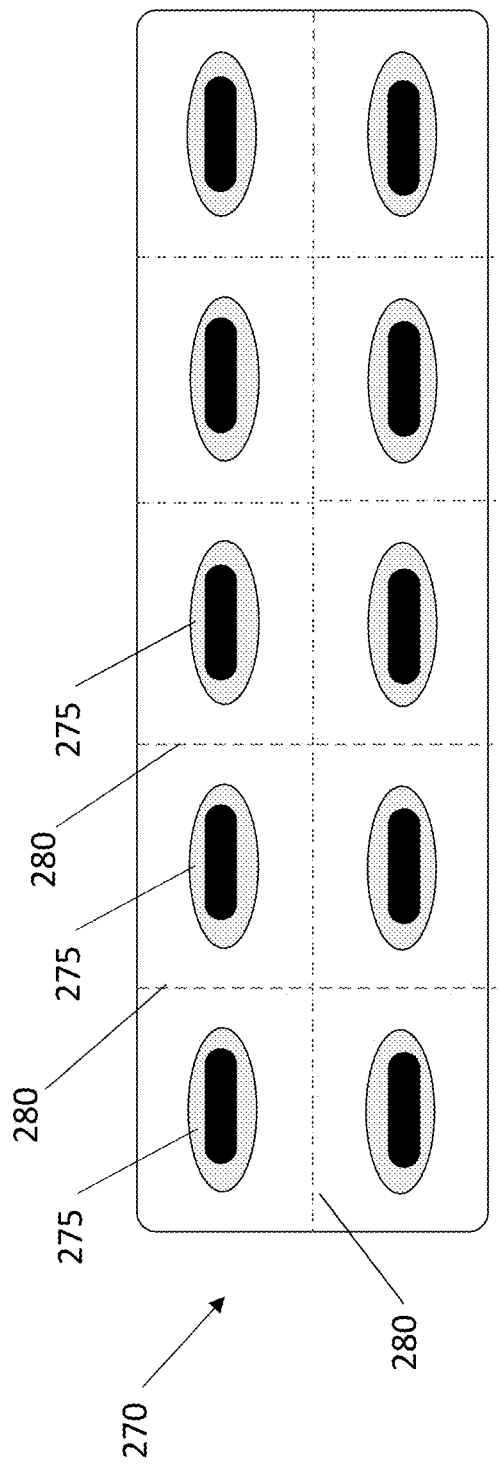
FIG. 25 illustrates an example embodiment of a blister pack card including a plurality of blister packs.

FIG. 24 illustrates an automated dispensing system 200 that further includes an auto singulator device 268. Articles, such as medications, may be received in packaging that requires manipulation or separation prior to storing in the storage modules 202. For example, medications may be received in a blister package format. When unit dose medications are packaged into a blister, they are typically packaged with several medication unit doses per blister card, such that there are a corresponding number of equally-spaced vinyl formed cavities per blister card. These cavities are typically separated by a perforation. A singulated blister is one that has been separated from a blister card, typically along its perforation. FIG. 25 illustrates a diagram of a blister card 270 according to an example embodiment. As shown, the blister card 270 may include a plurality of unit dose blisters 275 separated by perforations 280. The auto singulator 268 of example embodiments described herein may be configured to separate the unit dose blisters 275, generally along their perforations, to be in single unit dose form for storage within the storage module.

In practice, one or more blister cards 270 may be received at the auto singulator 268 of the automated dispensing system 200 of an example embodiment. The blister card 270 may be received directly from an operator or technician, or alternatively the blister card may be received via a restocking cart 220 at the cart station 218, whereupon the blister card 270 may be transported, via robot 204, to the auto singulator 268. Upon receipt at the singulator 268, the singulator may separate the blister card 270 into individual unit dose blisters 275. The unit dose blisters, may each have thereon a medication identification, otherwise the unit dose blisters may be repackaged into an overpack, or receive thereon a label identifying the medication of the unit dose blister. The identifiable unit dose blisters may then be retrieved by the robot 204, such as by the end-of-arm-tool 208, and moved to storage locations within the trays 212 as determined by a storage optimization tool at the controller.

Figure 26:
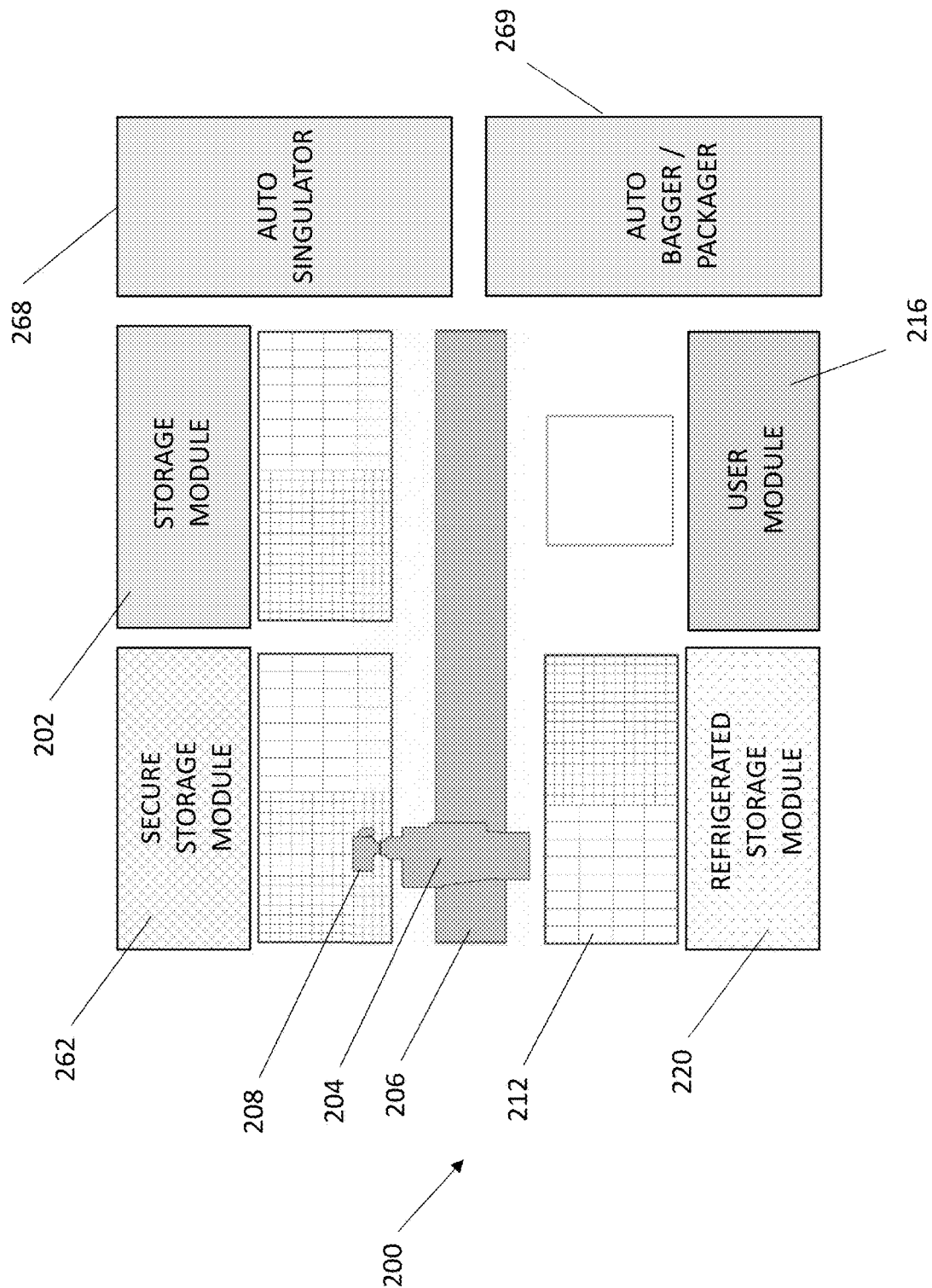
FIG. 26 illustrates a plan view of a modular automated dispensing system having an automated packaging module according to an example embodiment of the present invention.

The modular nature of the automated dispensing system 200 of example embodiments enables the expansion of the system to include various other modules that may facilitate dispensing. Beyond those modules described above, another such module is an automated bagger or automated packager 269 as illustrated in FIG. 26. The automated packager may receive articles that are retrieved for dispensing from the end-of-arm tool 208 of the robot 204 and package them into an overpack appropriate for the destination and contents of the package. For example, if a patient in a healthcare facility is to receive one or more unit doses of medications that are packaged in blister packs, the automated dispensing system 200 may retrieve those medication blister packages, and advance them to the auto packager 269. The medication blister packs may be received within a bag, or within a staging area of the auto packager from which they are dispensed into a bag. The bag may be printed with the patient's name, a patient location (e.g., room number), or other identifying information. The bag or other packaging may also be printed with a time at which the medications contained therein are to be dispensed to the patient.

The automated packaging module 269 may be equipped with a printer configured to print a label in response to the automated dispensing system dispensing articles of a particular order. The label may be printed in response to the dispensing process starting, or upon receipt of the articles at the auto packaging station 269. The dispensing process may involve scanning (e.g., scanning a barcode or RFID tag) or otherwise identifying the retrieved articles and correlating them with an order for those retrieved articles. The identification may be performed by a scanner attached to the end-of-arm tool 208, the vial roller described above, or an identification station to which an articles is moved by the robot 204 and end-of-arm tool 208 for identification. In this manner, the articles may be positively identified at one or more stages throughout the dispensing process in order to ensure the appropriate articles are dispensed for each order received. Orders may be filled individually in sequence, or simultaneously. The controller, as described above, may optimize the dispensing process, such as filling multiple orders for the same article concurrently. Regardless, the systematic identification of articles throughout the process may be used to ensure the appropriate articles are dispensed to the appropriate packaging at the auto packaging station 269 with one or more verification steps along the way to ensure accuracy.

Once the auto packaging module 269 has packaged or bagged the dispensed articles, the articles may be ready for distribution. The packaged articles may be retrieved directly from the auto packaging station 269, for example, by an operator. Or the automated packaging station 269 may be configured to package the articles such that the package may be retrieved by the robot 204 using the end-of-arm-tool 208, and moved to the cart module in preparation for the cart to be retrieved by an operator with a plurality of filled orders.

While example embodiments above are directed to dispensing of medications according to orders received in the system in a systematic and generally first-in-first-out order/retrieval sequence, certain medication orders may require special attention which may include expediting a medication order. For example, first doses of medication or doses of medication which are new to a patient may require special attention. Unique carriers or carrier holders may be designated for receiving first doses in order to alert the operator that the medication on the unique carrier or carrier holder is a first dose, and should be treated accordingly with the appropriate care and consideration of the pharmacists, nurses, and doctors involved. The unique carriers or carrier holders could be identified by color coding or some other means that would alert the operator that the medication contained on these unique carriers or carrier holders are first doses. If a first dose of a medication was encountered in a medication order during the fill operation for a patient, the robot may complete the medication order without the first dose, and subsequently retrieve one of the unique carrier holders on which to place the first dose for that patient. Optionally, the automated dispensing system may include flags that may be placed on a carrier adjacent to a medication on the carrier to indicate that it is a first dose. For example, during the medication order fill, if a medication was determined to be a first dose, after loading the medication on the carrier the robot may load a first dose flag onto the carrier indicating to the operator that the dose behind that flag is a first dose and should be handled accordingly.

End-of-Arm-Tool

Figure 27:
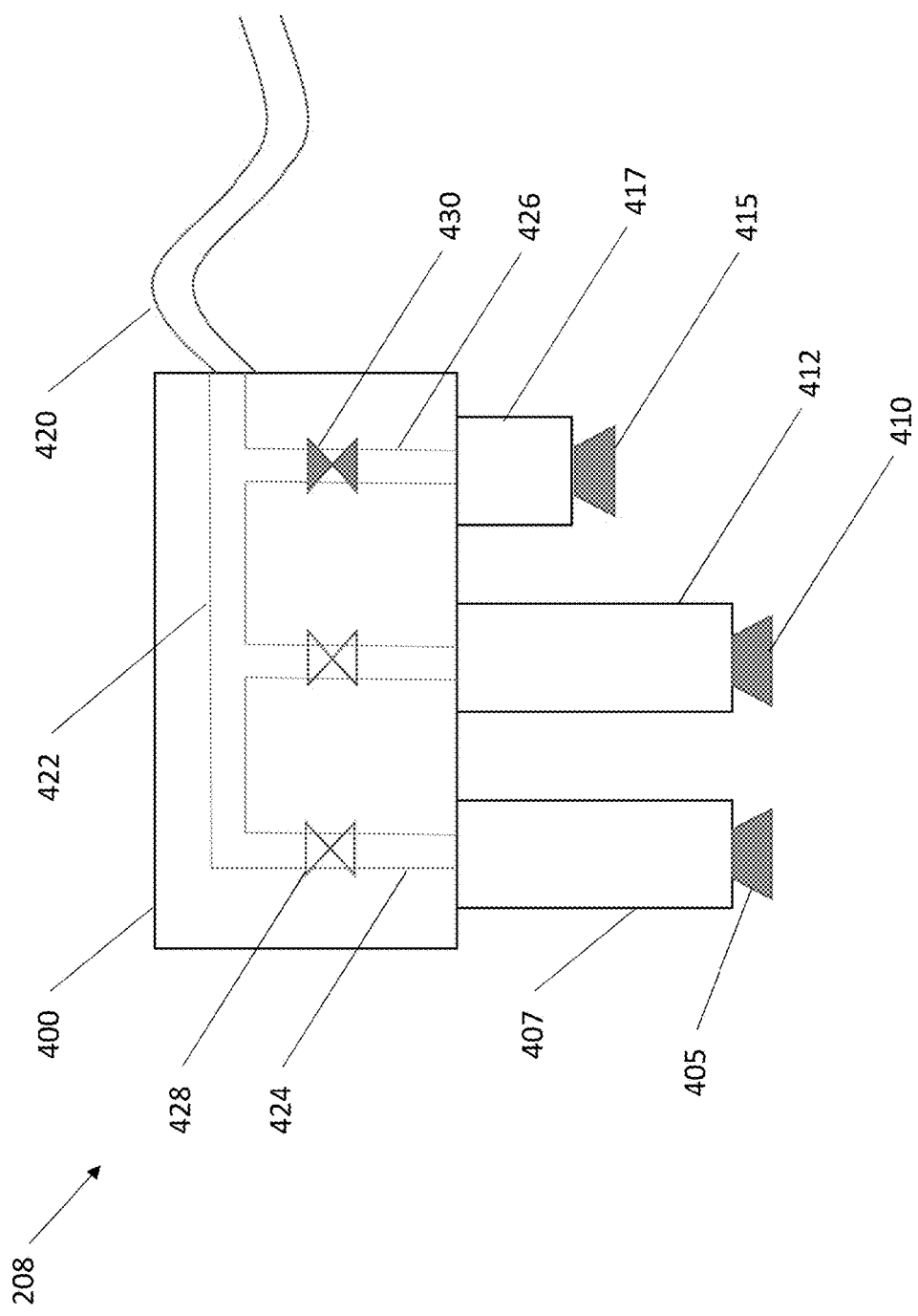
FIG. 27 illustrates an end-of-arm tool according to an example embodiment of the present invention.

As described above, the automated dispensing system 200 of example embodiments may include a robot 204. The robot may be a multi-axis arm with a wide range of motion and several degrees of freedom. The robot 204 may be equipped with an end-of-arm tool 208, such as the example embodiment illustrated in FIG. 27. The illustrated embodiment includes an end-of-arm tool body 400 from which vacuum cups 405, 410, and 415 extend on extending members 407, 412, and 417, respectively. The end-of-arm tool body 400 may be supplied with a vacuum source via conduit 420. The vacuum may be generated by a pump, which may be collocated with the robot 204 and travel with the robot along the track system 206. Optionally, the pump may be located remotely from the robot and track system, and may include a vacuum hose that is included with the cables of the umbilical cable used to power and control the robot 204 by the controller.

Figure 28:
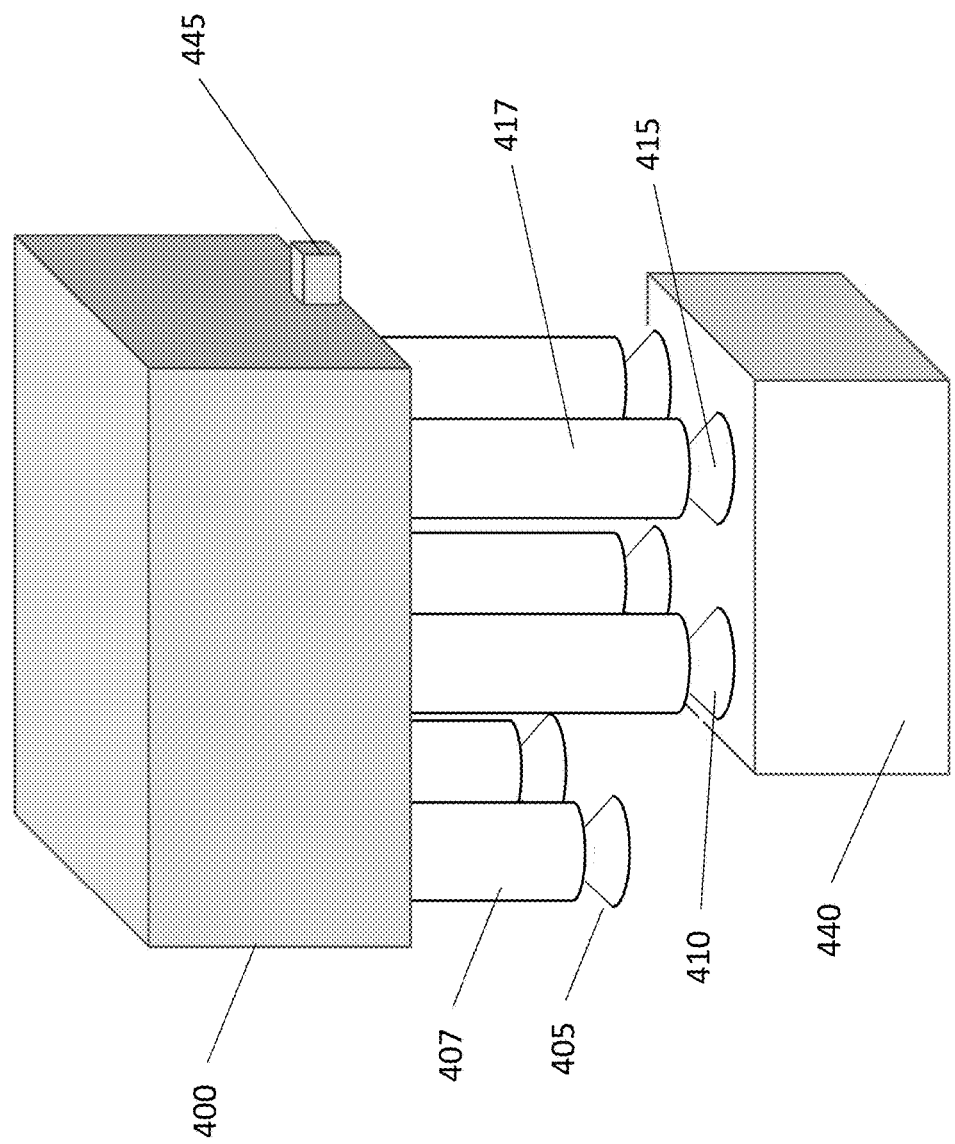
FIG. 28 illustrates another view of an end-of-arm tool according to an example embodiment of the present invention.
Figure 29:
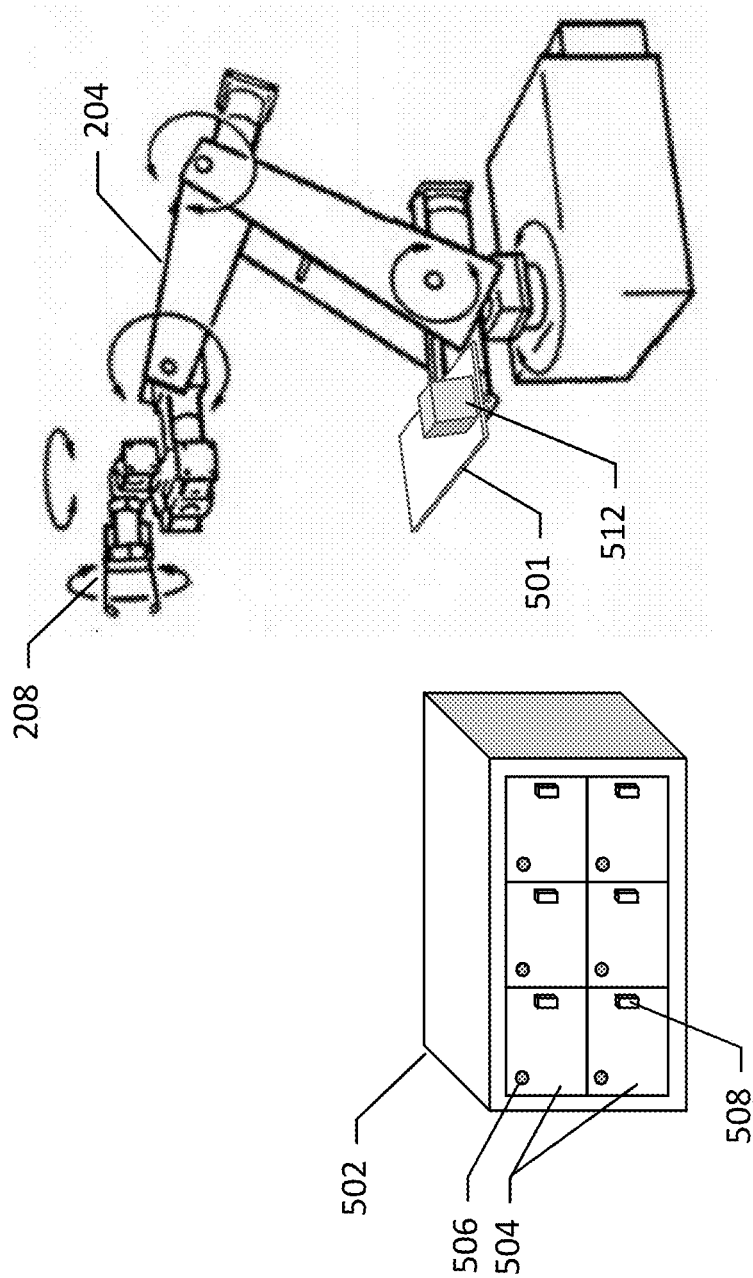
FIG. 29 illustrates an example end of arm tool configured with a gripper together with a secure retrieval cabinet.

While example embodiments described herein include an end-of-arm tool 208 configured to pick objects using vacuum, the end-of-arm tool may optionally be configured with a gripper, such as the gripper shown in FIG. 29. The gripper may be in addition to the end-of-arm tool 208 of FIGS. 27 and 28 to increase the functionality of the robot 204 of systems described herein.

The controller, which may be the controller used to control the robot 204 and other components of the dispensing system illustrated in FIG. 12, or may be a separate controller used exclusively to control the end-of-arm tool 208, which may be directed or instructed by the controller of the automated dispensing system. The end-of-arm tool 208 may include within or attached to the body 400 a manifold to which the vacuum source 420 is attached. This manifold 422 may be in communication with a vacuum channel 424, 426, for each vacuum cup 405. A valve 428, 430 may control the vacuum flow from the manifold 422 to each vacuum cup 405, 410, and 415. In this manner, the controller may independently control the valves 428, 430 in order to apply a vacuum to a vacuum cup or to preclude a vacuum from being applied to a vacuum cup. The controller may select one or more of the plurality of vacuum cups to supply a vacuum to, and close the valves associated with each of the other vacuum cups. Optionally, the valves 428, 430, may not be binary on/off valves and may allow partial opening/closing to reduce the vacuum flow through a particular vacuum cup, as needed.

The vacuum cups 405, 410, 415, of example embodiments may be a flexible rubber or plastic to enable the vacuum cups to engage a product and to create a seal against the product. The vacuum cups may be of different sizes to accommodate engaging different surfaces. For example, a cylindrical vial that is engaged along its curved length may not be compatible with a large vacuum cup as the large vacuum cup may be incapable of creating a sufficient seal on a vial of a relatively small diameter. Conversely, a relatively smaller vacuum cup may be able to establish a seal with the vial sufficient to allow the end-of-arm tool 208 to pick up and move the vial.

Each of the vacuum cups 405, 410, and 415, may be attached to extending members 407, 412, and 417, respectively. These extending members may extend from the end-of-arm tool body 400. A solenoid (not shown) may be attached to each extending member within the end-of-arm tool body 400 to move the extending members to move each extending member between an extended position (illustrated by extending members 407 and 412) or a retracted position (illustrated by extending member 417), independently. The retraction/extension of extending members may optionally be controlled by a pneumatic solenoid, where in response to the vacuum being shut off from a vacuum cup of a particular extending member, the vacuum is instead diverted to the pneumatic solenoid to raise the extending member to the retracted position.

FIG. 28 illustrates an example embodiment of an end-of-arm tool 208 of a robot 204 (not shown) as engaged with an article 440. According to the illustrated embodiment, extending member 407 and associated vacuum cup 405 is in the retracted state, as is an extending member and vacuum cup disposed behind it. Four extending members including 417 are disposed in the extended position with vacuum cups (including 410, 417) engaging the article 440. As the article is not of sufficient size to require or engage vacuum cup 405, vacuum cup 405 is determined to not be required for engaging the article, and it is moved to the retracted position. The determination of which vacuum cups to use and which extension members to retract may be performed by the controller. The controller may determine, based on the identification of an article to be retrieved and an associated packaging size, which may be stored, for example in memory 232, which vacuum cups are required to engage the article. For example, an article for retrieval may be requested, and the controller may reference a database of stored article configurations in the memory 232 using processor 230. The controller may determine the appropriate vacuum cups to use based on the stored configuration, and retract those that will be unused.

According to another example embodiment provided herein, the end-of-arm tool may be equipped with a scanner or reader, such as a barcode scanner or RFID reader, as illustrated as 445 of FIG. 28. The end-of-arm tool may determine the identification of the article to be retrieved based on a scan, and based on a known identification and configuration (e.g., stored in memory 232), the appropriate vacuum cups may be established and appropriate configuration of extending members may also be established.

While the varying sizes of articles can be accommodated through extension and retraction of the extending members, and the use of some or all of the vacuum cups, heavier objects may require greater vacuum to maintain engagement between the object and the end-of-arm tool. The weight of an object may be stored in the memory along with a packaging configuration or form factor such that a configuration of extension members and vacuum cups, along with their relative vacuum pressure may be established. Optionally, the memory may store a configuration of extension members, vacuum cups, and vacuum pressure for one or more articles. The vacuum level may be controlled by the valves of the end-of-arm tool (such as valves 428, 430), controlled by a pressure regulator governed by the controller, or optionally, controlled by the vacuum source (e.g., the pump).

The end-of-arm tool of example embodiments may be equipped to perform machine learning operations in cooperation with the controller. For example, when retrieving an object, a height of the object from a surface may not be known to the end-of-arm tool, such that the tool must advance toward the object and determine when contact is made. The height at which this contact is made may be recorded and stored for the particular article and package configuration such that subsequent retrievals of the article may use the stored height of the object to estimate the height of engagement of the end-of-arm tool with the object.

Some example embodiments provided herein may include articles with unknown packaging configurations, or the packaging configurations may not be consistent between similar articles. For example, when articles are in overpacks, two articles of the same identification may have different form factors. As such, an example embodiment provided herein may include an end-of-arm tool having a vision system configured to determine the form factor shape and size. The vision system may be included in 445 such that the shape and size of an article may be determined as the end-of-arm tool encounters the article. Based on the vision system scanning the article, the appropriate number and configuration of vacuum cups and extending members may be established, while the remaining vacuum cups (if any) may be retracted with their respective extending members.

Vision systems of example embodiments may be used to find a center point or centroid of an article to be retrieved. This may enable an end-of-arm tool to better establish where to locate retrieving features, such as suction cups, to avoid article imbalance or to mitigate potential drops. Vision systems described herein may further be configured to identify drawer locations, identify pockets within drawers, identify specific pockets using identifiers proximate those pockets, or the like. This may facilitate picking of articles from a pocket and stocking articles to a pocket.

According to one example embodiment, a vision system may use algorithms to detect articles and to estimate the orientation of those articles. Some products may be difficult to identify and locate, such as vials of clear liquid. A vision system may identify a cap to a vial, identify the plane of the cap then use any portion of the label to identify the axis along which the vial extends. The vision systems of example embodiments may be configured for machine learning to adapt to identifying products, particularly those products that are difficult to detect reliably, such as vials of clear liquid. The machine learning technique may optionally include user teaching whereby known articles are introduced to the system and identifications of those articles known to the system such that the vision system may view the article and establish the unique characteristics of each product, and potentially each brand of each product.

One or more of the vacuum cups and vacuum lines extending from the respective vacuum cups may include a vacuum gauge. Optionally, one vacuum gauge may be used for all of the vacuum cups of the end-of-arm tool. The vacuum gauge may be in communication with the controller as a feedback of the vacuum level at the end-of-arm tool and at one or more vacuum cups, depending upon the configuration. The vacuum gauge may be used to determine when an article is engaged by the vacuum cups. For example, a vacuum cup that is being used to engage an article may have a steady-state vacuum of a first level when not engaged with the article. Upon engaging and attaching to the article, the vacuum may increase to a second level, indicating that there is a sufficient seal of the vacuum cup on the article to draw vacuum. The controller may monitor the vacuum level of the one or more vacuum cups in order to determine if a sufficient vacuum is pulled across all of the vacuum cups attached to an article to pick up and move the article. If the vacuum level is too low, it may be an indication that one or more of the vacuum cups is not properly engaged with the article, and the end-of-arm tool may attempt to re-position on the article to align the vacuum cups with a surface to which they can engage.

The vacuum gauge may optionally be configured to identify a drop condition or an impending drop condition. After an article has been picked up by the end-of-arm tool, while the vacuum levels of the active vacuum cups are at a sufficient vacuum to indicate engagement, in response to the vacuum levels of one or more vacuum cups decreasing, an imminent drop condition may be established and the robot 204 may move the end-of-arm tool 208 to a location where the article may be re-engaged. In response to each of the vacuum level of each of the vacuum cups decreasing at substantially the same time, a drop condition may be detected and an alert may be generated at the user module to indicate to a user that an article has been dropped. If the article is dropped proximate a destination or a location of a tray (e.g., immediately above the destination or location), the article may be retrieved by the end-of-arm tool without necessarily alerting an operator.

The configuration of various articles may optionally be learned by a controller of an automated dispensing system of example embodiments. For example, if an article is identified and a vision system is used to determine the appropriate vacuum cup and extension member configuration, the reliability with which the article is moved (e.g., no dropped articles and no or few impending drop conditions), that configuration may be learned by the controller and stored to memory for use when retrieving an article of the same identification in the future. Adaptive learning in this manner may use a vision system as described above, while also building a database of known articles and known appropriate configurations. The machine learning aspects of the dispensing systems described herein may associate certain article identifiers with package types, package configurations, package sizes, and package weights. This may be retained in a table stored within the controller that is referenced when an object it to be retrieved. When retrieving an object, the table may be referenced to establish the anticipated details of the package. While this information may be beneficial to the system and the end-of-arm tool 208, the previously learned package information is not strictly relied upon as packaging types may change periodically. However, the learned package information may generally be accurate or provide sufficient guidance to the system and the robot 204 that the efficiency of article retrieval is substantially improved with learned packaging configurations.

As noted above, certain medication orders or exceptions require unique treatment. Medication orders that are first-dose orders or a quick-pick (or on-demand, STAT, etc.) may be handled differently than a conventional medication pick and dispensing operation. For such circumstances, the robot 204 and system 200 of example embodiments may include features to facilitate such first-dose or quick-pick orders. FIG. 29 illustrates an example embodiment of robot 204 that includes the end-of-arm tool 208. The robot 204 further includes work surface 510 and container 512 disposed on the work surface. The system 200 of example embodiments may include a first-dose/quick-pick retrieval area, which in the illustrated embodiment is a cabinet 502. The cabinet 502 may be included with any of the modules identified above in system 200, such as in user module 216. The cabinet 502 of FIG. 29 includes six storage lockers 504, each one having a handle 508 and an indicator 506. In practice, when an order is received for a first-dose or a quick-pick order that needs to be readied as soon as possible, the robot 204 may cease the operation it was previously performing to retrieve the necessary medication(s) for the first-dose or quick-pick. The robot 204 may retrieve the necessary medication(s), and for a single first-dose order or quick-pick order, may place the medications in container 512 on work surface 510. The robot 204 may then proceed to cabinet 502 and place the container 512 into one of the lockers. The lockers may be accessible to the robot 204 from within the modular system 200, but locked to prevent unauthorized access from outside of the system 200.

Upon placing the container 512 having the medication of the first-dose or quick-pick order into the cabinet, the order may be ready for retrieval. In some circumstances, an alert may be provided by the system that the order is ready to be retrieved. A user may access the medication order by entering their identification into the user interface of the system 200 and specifying the order they wish to retrieve. As noted above, the cabinet may have an indicator 506 for each door 504, and the indicator associated with the medication to be retrieved may be illuminated, alerting the user of the locker in which their order is located. The door 504 may be unlocked to allow access to the medication order by the authorized user. Optionally, the doors 504 may be numbered or otherwise identified and the user interface of the system 200 may direct the user to the appropriate door to retrieve their medication without requiring an indicator 206.

According to some embodiments, upon entry of the user identification and identification of the order that they are retrieving, a label for that order may be printed at the user module 216. Regardless of the number of orders that a user may be retrieving, only a label or labels for the order to be retrieved is printed, and the system 200 may await retrieval of the associated first-dose or quick-pick medication from the cabinet 502. The retrieval process including the unlocking of the respective door 504 may await a scan of the printed label to confirm that the user has retrieved the label and needs only the associated medication in order to marry the label to the correct medication. Once the medication is retrieved and the respective door 504 closed, the user may enter another order that they are to retrieve, and a label for that order may be printed. This order of operations ensures that multiple labels and multiple orders are not printed and retrieved simultaneously, increasing the chances of a mislabeled medication.

Figure 30:
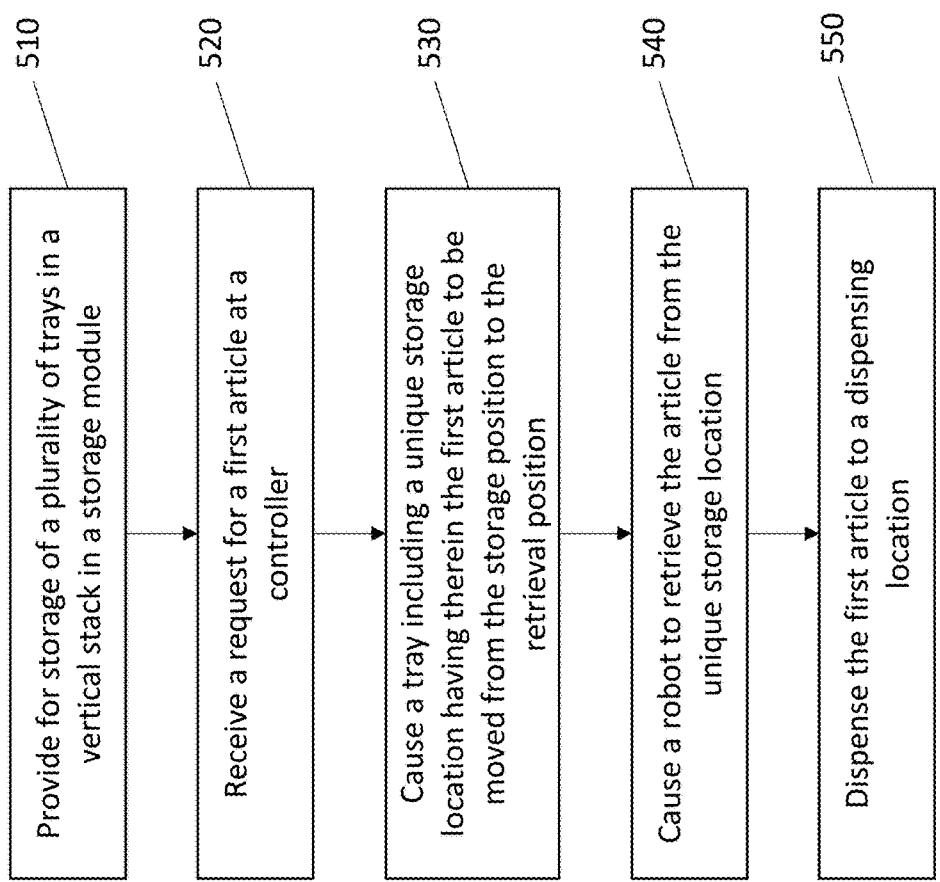
FIG. 30 illustrates is a flowchart of a method of operating an automated dispensing system according to an example embodiment of the present invention.

FIG. 30 is a flowchart of a method and program product according to an example embodiment of the present invention. It will be understood that each block of the flowchart and combinations of blocks in the flowchart may be implemented by various means, such as hardware, firmware, processor, circuitry, and/or other devices associated with execution of software including one or more computer program instructions. These computer program instructions may also be stored in a non-transitory computer-readable memory that may direct a computer or other programmable apparatus to function in a particular manner, such that the instructions stored in the computer-readable memory produce an article of manufacture which implements the functions specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the invention, as shown in FIG. 30, may include providing for storage of a plurality of trays in a vertical stack in a storage module as shown at 510. A request for a first article may be received at 520, such as via the controller. The request may be generated by a system such as a healthcare facility patient management system and communicated to the controller over a communication network. At 530, a tray including a unique storage location having therein the first article may be caused to move from the storage position to the retrieval position. This movement may be effected by a solenoid or drive motor within the storage module, or alternatively the robot may move the tray. At 540, the robot may be caused to retrieve the article from the unique storage location, and to dispense the article to a dispensing location as shown at 550.

In some embodiments, certain ones of the operations may be modified or further amplified as described below. Moreover, in some embodiments additional operations may also be included. It should be appreciated that each of the modifications, optional additions, or amplifications below may be included with the operations above either alone or in combination with any others among the features described herein.

In an example embodiment, an apparatus for performing the method of FIG. 28 may include a processor configured to perform some or all of the operations (510-550) described above. The processor may, for example, be configured to perform the operations (510-550) by performing hardware implemented logical functions executing stored instructions, or executing algorithms for performing each of the operations. Alternatively, the apparatus may include means for performing each of the operations described above.

An example of an apparatus according to an example embodiment may include at least one processor and at least one memory including computer program code. The at least one memory and the computer program code may be configured to, with the at least one processor, cause the apparatus to perform the operations 510-550.

An example of a computer program product according to an example embodiment may include at least one computer-readable storage medium having computer-executable program code portions stored therein. The computer-executable program code portions may include program code instructions for performing operations 510-550.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An automated dispensing system comprising:
a controller configured to process a request for one or more articles to be dispensed;
one or more storage modules comprising a plurality of moveable trays stacked vertically, each of the moveable trays comprising one or more storage locations to hold the one or more articles;
a loading bin having an end panel and a sliding floor; and
a robot configured to access the one or more storage locations within the one or more moveable trays within the one or more storage modules and transfer the requested one or more articles to the loading bin prior to dispensing the requested one or more articles from the loading bin into a patient-specific container,
wherein each of the one or more moveable trays is moved from a storage position to a retrieval position prior to the access by the robot to the one or more storage locations to retrieve the one or more articles,
wherein the loading bin dispenses the requested one or more articles into the patient-specific container in response to the loading bin being inserted into the patient-specific container, the end panel opening an end of the bin, the sliding floor retracting from the bin, and the bin being removed from the patient-specific container.

2. The automated dispensing system of claim 1, wherein one of the one or more storage modules includes an upper closure door and a lower closure door adapted to enable the robot to access the one or more trays between the upper closure door and the lower closure door.

3. The automated dispensing system of claim 2, wherein an adjustable opening is defined between the upper closure door and the lower closure door and sized to permit movement of the one or more trays through the opening.

4. The automated dispensing system of claim 3, wherein the adjustable opening is movable between a bottom most tray on a particular storage module and an uppermost tray on the particular storage module.

5. The automated dispensing system of claim 1, wherein at least one of the one or more storage modules is insulated and adapted to allow control of temperature within the storage module.

6. The automated dispensing system of claim 1, wherein at least one of the one or more storage modules is a secure storage module that controls access to the contents of the secure storage module for a user.

7. The automated dispensing system of claim 6, wherein the automated dispensing system is configured to enable user access within the automated dispensing system, and wherein the secure storage module restricts access to the contents of the secure storage module in response to a user entering the automated dispensing system.

8. The automated dispensing system of claim 7, wherein access to the secure storage module is controlled by the controller.

9. The automated dispensing system of claim 1, wherein at least one of the one or more storage modules comprises a tray elevator configured to move any of the one or more trays within the at least one storage module from a retrieval position to an access position, wherein the access position of the tray is closer to the robot than the retrieval position of the tray.

10. The automated dispensing system of claim 1, wherein the robot is a first robot, the system further comprising a second robot, wherein the first robot and the second robot both traverse a single track.

11. The automated dispensing system of claim 10, wherein the first robot and the second robot are controlled by the controller to cooperate and increase throughput of the automated dispensing system.

12. The automated dispensing system of claim 1, further comprising a non-transitory memory, wherein the memory is configured to store a unique identification for each of the plurality of storage locations for each of the plurality of trays, and an identification of an article stored in each of the plurality of storage locations.

13. The automated dispensing system of claim 1, wherein at least one of the one or more trays comprises one or more tray inserts, each of the one or more tray inserts comprising at least a portion of the plurality of storage locations for the respective tray, wherein the system further comprises a cart module, wherein the cart module is configured to receive therein a cart holding a plurality of tray inserts, wherein tray inserts from the cart are exchanged by the system for tray inserts from a tray to replenish the automated dispensing system.

14. A method of operating an automated dispensing system, the method comprising:
receiving a request for dispensing one or more articles;
identifying unique storage locations for the one or more articles;
determining a selection sequence to enable the retrieval of the one or more articles;
moving one or more trays holding the one or more articles, to allow retrieval of the one or more articles, based on the selection sequence;
retrieving the one or more articles from their unique storage locations in the one or more trays;
temporarily storing the one or more articles in a loading bin associated with the request until all of the one or more articles in the request are retrieved;
inserting the loading bin into a patient-specific container;
raising an end of the loading bin;
retracting a sliding floor of the loading bin; and
withdrawing the loading bin from the patient-specific container leaving the one or more articles in the patient-specific container.

15. The method of claim 14, further comprising scanning each of the one or more articles prior to storing each of their one or more articles in their unique storage location and associating the one or more articles to their respective unique storage location.

16. The method of claim 15, wherein retrieving the one or more articles from their unique storage locations further comprising:
reading an identification of the unique storage location prior to retrieving each of the one or more articles.

17. An apparatus comprising at least one processor and at least one non-transitory computer readable storage medium comprising program code instructions stored thereon, the at least one processor configured to, upon execution of the program code instructions, cause the apparatus to at least:
receive a request to dispense one or more articles;
identify a unique storage location for the one or more articles;
determine a selection sequence to enable the retrieval of the one or more articles;
move one or more trays holding the one or more articles to a retrieval position based on the selection sequence;
retrieve the one or more articles from their unique storage locations in the one or more trays;
temporarily store the one or more articles in a loading bin associated with the request until each of the one or more articles in the request is retrieved;
insert the loading bin into a patient-specific container;
raise an end of the loading bin;
retract a sliding floor of the loading bin; and
withdraw the loading bin from the patient-specific container leaving the one or more articles in the patient-specific container.

18. The apparatus of claim 17, further comprising program code instructions to cause the apparatus to provide an indication upon completion of the request to dispense.

19. The apparatus of claim 17, further comprising program code instructions to cause the apparatus to transfer the one or more articles to a bagging device to collectively house the one or more articles in a storage container.

20. The apparatus of claim 19, further comprising program code instructions to print information pertaining to the one or more articles of the request.

21. The apparatus of claim 17, further comprising program code instructions to cause the tray including the unique storage location to be moved from the retrieval position to an access position by a tray elevator, wherein movement from the storage position to the retrieval position is along a first axis, and wherein movement from the retrieval position to an access position is along a second axis, perpendicular to the first axis.

* * * * *